United States Patent
Nørgaard et al.

(10) Patent No.: US 8,518,668 B2
(45) Date of Patent: *Aug. 27, 2013

(54) METHOD FOR MAKING MATURATED INSULIN POLYPEPTIDES IN A FUNGAL CELL

(75) Inventors: Per Nørgaard, Humlebæk (DK); Asser Sloth Andersen, Herlev (DK)

(73) Assignee: Novo Nordisk A/S, Bagsvaerd (DK)

( * ) Notice: Subject to any disclaimer, the term of this patent is extended or adjusted under 35 U.S.C. 154(b) by 397 days.

This patent is subject to a terminal disclaimer.

(21) Appl. No.: 12/311,431

(22) PCT Filed: Sep. 26, 2007

(86) PCT No.: PCT/EP2007/060209
§ 371 (c)(1),
(2), (4) Date: Mar. 25, 2009

(87) PCT Pub. No.: WO2008/037735
PCT Pub. Date: Apr. 3, 2008

(65) Prior Publication Data
US 2010/0184133 A1    Jul. 22, 2010

Related U.S. Application Data

(60) Provisional application No. 60/853,661, filed on Oct. 23, 2006.

(30) Foreign Application Priority Data

Sep. 27, 2006 (EP) .................................... 06121346

(51) Int. Cl.
C12N 1/15      (2006.01)
C12N 15/17     (2006.01)
C12P 21/06     (2006.01)

(52) U.S. Cl.
USPC ...................... 435/69.7; 435/68.1; 435/254.1

(58) Field of Classification Search
None
See application file for complete search history.

(56) References Cited

U.S. PATENT DOCUMENTS

| | | | |
|---|---|---|---|
| 4,914,026 A | 4/1990 | Brake et al. | |
| 6,337,194 B1 | 1/2002 | Hadfield et al. | |
| 6,348,327 B1 | 2/2002 | Gorman et al. | |
| 8,153,395 B2 * | 4/2012 | Nørgaard ..................... | 435/68.1 |
| 2003/0104981 A1 | 6/2003 | Mandic | |

FOREIGN PATENT DOCUMENTS

| EP | 0163529 | 12/1985 |
|---|---|---|
| WO | 90/01038 A1 | 2/1990 |
| WO | WO 90/10075 | 9/1990 |
| WO | 90/12814 A1 | 11/1990 |
| WO | WO 95/02059 | 1/1995 |
| WO | WO 95/35384 | 12/1995 |
| WO | WO 97/03089 | 1/1997 |
| WO | 01/49870 A1 | 7/2001 |
| WO | 02/079250 | 10/2002 |
| WO | WO 2007/020256 | 2/2007 |
| WO | WO2008/037735 | 4/2008 |

OTHER PUBLICATIONS

Todd R. Graham et al., Compartmental Organization of Golgi-Specific Protein Modification and Vacuolar Protein Sorting Events Defined in a Yeast SEC18 (NSF) Mutant, The Journal of Cell Biology. vol. 114(2), pp. 207-218 (1991).
Bevan, A. et al., "Quantitative Assessment of Enzyme Specificity in vivo: $P_2$ Recognition by Kex2 Protease Defined in a Genetic System", Proc. Natl. Acad. Sci. USA, 1998, vol. 95, pp. 10384-10389.
Frank, B.H. et al., The Production of Human Proinsulin and its Transformation to Human Insulin and C-Peptide, 1981, pp. 729-738.
Hopkins, B.D. et al., "Introduction of Kex2 Cleavage Sites in Fusion Proteins for Monitoring Localization and Transport in Yeast Secretory Pathway", Methods in Enzymology, 2000, vol. 327, pp. 107-118.
Hunt, S.M.N. et al., "Processing of Mutated Human Proinsulin to Mature Insulin in the Non-Endocrine Cell Line, CHO", Cytotechnology, 1996, vol. 21, pp. 279-288.
Kjeldsen, T., Yeast Secretory Expression of Insulin Precursors, Appl. Microbiol. Biotechnol., 2000,vol. 54, pp. 277-286.
Rockwell, N.C. et al., "Interplay Between $S_1$ an d $S_4$ Su bsites in Kex2 Protease: Kex2 Exhibits Dual Specificity for the P4Sid e Chain", Biochemistry, 1998, vol. 37, pp. 3386-3391.
Thim, L. et al., "Secretion and Processing of Insulin Precursors in Yeast", Proc. Natl. Acad. Sci. USA, 1986, vol. 83, pp. 6766-6770.
Thim, L. et al., "Secretion of Human Insulin by a Transformed Yeast Cell", FEBS Letters, 1987, vol. 212, No. 2, pp. 307-312.
Chu Ying-Chi et al, Journal of Protein Chemistry, "The A14 Position of Insulin Tolesrates Considerable Structural Alterations With Modest Effects on the Biological Behavior of the Hormone", 1992, vol. 11, No. 5, pp. 571-577.
Claus Kristensen et al., Journal of Biological Chemistry, "Alanine Scanning Mutagenesis of Insulin", 1997, vol. 272, No. 20, pp. 12978-12983.

(Continued)

*Primary Examiner* — Christine J Saoud
(74) *Attorney, Agent, or Firm* — Jianjie Hu

(57) ABSTRACT

The invention is related to a method for making mature human insulin or an analogue thereof by culturing a fungi cell comprising a DNA sequence encoding a precursor for human insulin or an analogue of human insulin which precursor comprises the B-chain of human insulin or an analogue thereof, the A-chain of human insulin or an analogue thereof and a C-peptide linking the B-chain and the A-chain together thereof, wherein the C-peptide comprises at least one Kex2 cleavage site and an amino acid sequence attached at one end to the C-terminal amino acid residue in the B-chain and at the other end to the Kex2 site which amino acid sequence will facilitate a more efficient Kex2 cleavage within the fungi cell. The C-terminal extension of the B-chain may furthermore be capable of subsequently being cleaved off from the C-terminal amino acid residue in the B-chain by means of a carboxypeptidase activity either within the fungi cell or subsequently in the culture medium.

9 Claims, 3 Drawing Sheets
(3 of 3 Drawing Sheet(s) Filed in Color)

(56) References Cited

OTHER PUBLICATIONS

Frank, Pettee, Zimmerman and Burck, Rich, Gross, Pierce Chemical Company. Rockford Illinois, "The Production of Human Proinsulin and Its Transformation to Human Insulin and C-Peptides", 1981, Volume -, No. -, pp. 729.

Kjeldsen, T et al, The Journal of Biological Chemistry, "Engineering-Enhanced Proitein Secretory Expression in Yeast With Application to Insulin", 2002, vol. 277, No. 21, pp. 18245-18248.

Olsen HB et al, Journal of Molecular Biology, "The Relationship Between Insulin Bioactivity and Structure in the NH2-Terminal A-Chain Helix", 1998, vol. 284, No. 2, pp. 477-488.

Weiss et al, Journal of Biological Chemistry, "Activities of Monomeric Insulin Analogs at Position A8 are Uncorrelated With Their Thermodynamic Stabilities", 2001, vol. 276, No. 43, pp. 40018-40024.

* cited by examiner

Figure 1

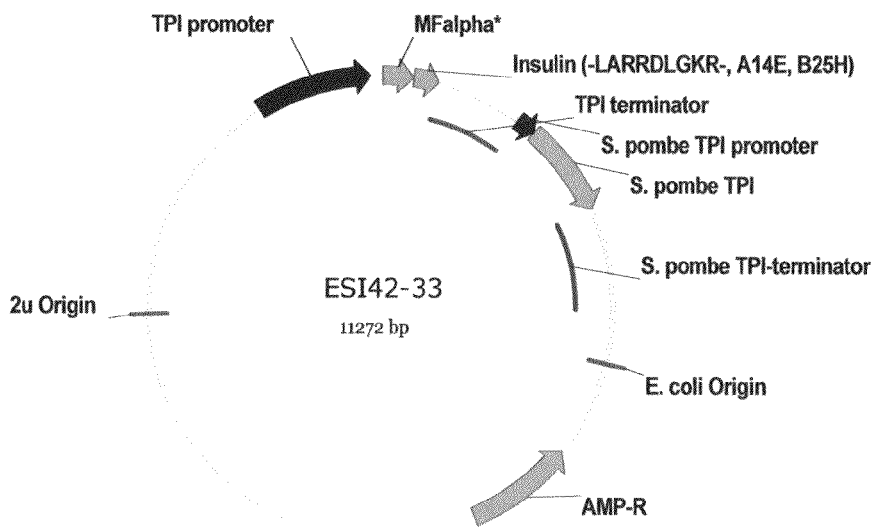

Figure 2

```
    NcoI

~~~~~~

SerMet AlaLysArg PheValAsnGln HisLeuCys GlySerHis LeuValGluAla
    CCAT GGCTAAGAGA TTCGTTAACC AACACTTGTG CGGTTCCCAC TTGGTTGAAG
    GGTA CCGATTCTCT AAGCAATTGG TTGTGAACAC GCCAAGGGTG AACCAACTTC

LeuTyrLeu ValCysGly GluArgGlyPhe HisTyrThr ProLysThr LeuAlaArgArg
CTTTGTACTT GGTTTGCGGT GAAAGAGGTT TCCACTACAC TCCTAAGACT CTAGCGAGAA
GAAACATGAA CCAAACGCCA CTTTCTCCAA AGGTGATGTG AGGATTCTGA GATCGCTCTT

AspLeuGly LysArgGly IleValGluGln CysCysThr SerIleCys SerLeuGluGln
GAGACTTGGG TAAGAGAGGT ATTGTCGAAC AATGCTGTAC ATCGATATGC TCCTTGGAAC
CTCTGAACCC ATTCTCTCCA TAACAGCTTG TTACGACATG TAGCTATACG AGGAACCTTG
                                  XbaI
                                ~~~~~~~
  LeuGluAsn TyrCysAsn ***
AATTGGAAAA CTACTGCAAC TAGACTCTAG A
TTAACCTTTT GATGACGTTG ATCTGAGATC T
```

METHOD FOR MAKING MATURATED INSULIN POLYPEPTIDES IN A FUNGAL CELL

CROSS-REFERENCE TO RELATED APPLICATIONS

This application is a 35 U.S.C. §371 national stage application of International Patent Application PCT/EP2007/060209 (published as WO 2008/037735 A1), filed Sep. 26, 2007, which claimed priority of European Patent Application 06121346.8, filed Sep. 27, 2006; this application further claims priority under 35 U.S.C. §119 of U.S. Provisional Application 60/853,661, filed Oct. 23, 2006.

FIELD OF THE INVENTION

The present invention is related to a process for making mature insulin or insulin analogues in yeast.

INCORPORATION-BY-REFERENCE OF THE SEQUENCE LISTING

In accordance with 37 C.F.R. §1.52(e)(5), Applicants enclose herewith the Sequence Listing for the above-captioned application entitled "SEQUENCE LISTING", created on Feb. 20, 2009. The Sequence Listing is made up of 43 bytes, and the information contained in the attached "SEQUENCE LISTING" is identical to the information in the specification as originally filed. No new matter is added.

BACKGROUND OF THE INVENTION

Insulin is a polypeptide hormone produced in the beta cells of the islets of Langerhans. The active insulin molecule is a two-chain molecule consisting of a B- and an A-chain connected by two disulphide bridges. The insulin is synthesized as a precursor molecule proinsulin with the structure B-C-A wherein the C-peptide chain connects the C-terminal amino acid residue in the B-chain with the N-terminal amino acid residue in the A-chain. Mature two-chain insulin is formed by in vivo cleavage of the C-peptide at the pair of basic amino acid residues situated at the junction with the A- and B-chain. The A- and B-chain are held together by two disulphide bridges between the A7 and B7 and the A20 and B19 Cys residues, respectively. In addition, the biologically active insulin molecule has an internal disulphide bridge between the Cys residues in the position A6 and A11.

After the development of recombinant DNA technology numerous methods have been described to produce insulin and precursors thereof in genetically modified host cells. As E. coli does not have the cellular machinery for folding the expressed polypeptide and establish the disulphide bridges connecting the A- and B chain in the mature insulin this strategy includes a number of in vitro processing steps such as in vitro establishment of the disulphide bridges during refolding and subsequent cleavage of the C-peptide.

In contrast to E. coli eukaryotes contain the necessary machinery for folding and establishing disulphide bridges and thus would seem to be good candidates for production of mature insulin in genetically modified organisms. Numerous of yeast processes have been developed to produce insulin. In most of these processes a precursor of insulin with either the natural C-peptide or with a modified C-peptide are expressed and secreted from the yeast cell. WO 9535384 discloses such methods. The precursor molecules may comprise an N-terminal extension of the insulin B-chain. The modified C-peptide and the possible N-terminal extension of the B-peptide are designed not to be cleaved in the yeast cell and thus the precursors are secreted as single chain peptides wherein the A- and the B-chain are still connected by the modified C-peptide but with correctly positioned disulphide bridges. The mature insulin or insulin analogue product is then obtained in a number of subsequent in vitro enzymatic steps by cleavage of the C-peptide and possibly the N-terminal extension. These enzymatic steps are time consuming, often costly and introduce additional impurities that subsequently have to be removed in further downstream process steps like expensive chromatography steps and the like.

Thim et al, Proc Natl. Acad. Sci. USA, volume 83, 6766-6770 and Thim et al, in FEBS Letters, volume 212, number 2, 307-312 disclose expression of human proinsulin and a number of insulin precursors with certain modified C-peptides. Furthermore, WO 97/03089 disclose expression of insulin precursors with the formula BZA wherein B and A are the A and B peptide chains of human insulin being linked by at least one disulphide bond and Z is a polypeptide comprising at least one proteolytic cleavage site. However, the disclosed insulin precursors only give rise to minute amounts of secreted mature insulin in the culture medium.

A process for making mature insulin in genetically engineered animal cells that are not naturally capable of forming secretory granules is disclosed in U.S. Pat. No. 6,348,327.

The purpose of the present invention is to develop a fungi strain capable of producing fully processed mature insulin or insulin analogues in high yields so that expensive and time consuming downstream purification process steps are avoided.

SUMMARY OF THE INVENTION

In one aspect the present invention is related to a method for making mature human insulin or an analogue thereof by culturing a fungi cell comprising a DNA sequence encoding a precursor for human insulin or an analogue of human insulin which precursor comprises the B-chain of human insulin or an analogue thereof, the A-chain of human insulin or an analogue thereof and a C-peptide linking the B-chain and the A-chain together and comprising at least one Kex2 cleavage site, wherein the B-chain comprises a C-terminal extension facilitating more efficient Kex2 cleavage within the fungi cell, provided that if the B-chain only contains one Kex2 cleavage site then first amino acid residue in the C-terminal extension counted from the N-terminal end is not a Met residue, and isolating the expressed product from the culture medium.

In one embodiment the C-terminal extension of the B-chain is 2-5 amino acid residues long.

In another embodiment the C-terminal extension of the B-chain is 2-4 amino acid residues long.

In another embodiment the C-terminal extension of the B-chain is 2-3 amino acid residues long.

In another embodiment the C-terminal extension of the B-chain consists of 2 amino acid residues.

The amino acid residues in the C-terminal extension may be the same or different.

In one embodiment the amino acid residues in the C-terminal extension of the B-chain are the same or different hydrophobic amino acid residues selected from the group consisting of Phe, Leu, Ile, Tyr, Trp, Val, Met and Ala.

In another embodiment the amino acid residues in the C-terminal extension of the B-chain are hydrophobic amino acid residues selected from the group consisting of Phe, Leu, Ile, Val and Ala.

In another embodiment the first amino acid residue in the C-terminal extension of the B-chain counted from the N-terminal end is Leu.

In one embodiment the N-terminal extension of the B-chain is attached directly to the Kex2 site in the C-peptide.

In one embodiment the C-terminal extension of the B-chain is capable of subsequently being cleaved off by means of a carboxypeptidase activity either within the fungi cell or in the culture medium.

In a further embodiment the C-terminal extension of the B-chain is subsequently cleaved off by means of a carboxypeptidase giving mature human insulin or an analogue thereof.

Thus one embodiment of the invention is a method for making mature human insulin or an analogue thereof by 1) culturing a fungi cell comprising a DNA sequence encoding a precursor for human insulin or an analogue of human insulin which precursor comprises the B-chain of human insulin or an analogue thereof, the A-chain of human insulin or an analogue thereof and a C-peptide linking the B-chain and the A-chain together and comprising at least one Kex2 cleavage site, wherein the B-chain comprises a C-terminal extension facilitating more efficient Kex2 cleavage within the fungi cell, provided that if the B-chain only contains one Kex2 cleavage site then first amino acid residue in the C-terminal extension counted from the N-terminal end is not a Met residue, 2) cleavage of the C-terminal extension of the B-chain either adding a carboxypeptidase to the culture medium or by means of an endogenous carboxypeptidase and 3) isolating the mature insulin product from the culture medium.

The carboxypepidase enzyme may be any carboxypeptidase enzyme capable of efficient removal of the C-terminal extension of the B-chain. A well suited enzyme is the carboxypeptidase Y enzyme (CPY).

If the CPY is an endogenous CPY the endogenous gene encoding CPY is over expressed and is secreted to the culture medium.

In one embodiment the C-peptide comprises two Kex2 cleavage sites linked by at least one amino acid residue.

In a further embodiment the two Kex2 sites are linked by a peptide chain with from 1 to about 35 amino acid residues.

In another embodiment the Kex2 sites are linked by a peptide chain with from 1 to 10 amino acid residues.

In another embodiment the Kex2 sites are linked by a peptide chain with from 1 to 5 amino acid residues.

In another embodiment the Kex2 sites are linked by a peptide chain with from 2-10, from 2-8, from 2-7, from 2 to 6, from 2-5 or from 2-4 amino acid residues.

In another embodiment the Kex2 sites are linked by a peptide chain with 3-5 amino acid residues.

In one embodiment the peptide chain linking the two Kex2 sites has the sequence DLG, DDLG (SEQ ID NO:1) or DDDLG (SEQ ID NO:2).

In another embodiment the C-peptide comprises a single Kex2 cleavage site attached to the N-terminal amino acid residue in the A-chain, In another embodiment the C-peptide comprises a single Kex2 site and an amino peptidase cleavage site interposed between the Kex2 site and the N-terminal amino acid residue of the A-chain.

In another embodiment the insulin precursor has the sequence

B-$X_1$-$X_2$-Z-$X_3$-$X_4$-A where B is the B-chain of human insulin or an analogue thereof, A is the human insulin A chain or an analogue thereof, $X_1$ is a peptide sequence of 1-5 amino acid residues which may be the same or different and which will facilitate a more efficient Kex2 cleavage within the fungi cell, $X_2$ is a Kex2 cleavage site, Z is a peptide sequence with from 1 to about 35 amino acid residues or a peptide bond, $X_3$ is a Kex2 cleavage site or a peptide bond and $X_4$ is an aminopeptidase cleavage site or a peptide bond provided that if $X_3$ and $X_4$ are both a peptide bond then the first amino acid residue in $X_1$ from the N-terminal end is not a Met residue.

In another embodiment $X_1$ is 2-5 amino acid residues long.
In another embodiment $X_1$ is 2-4 amino acid residues long.
In another embodiment $X_1$ is 2-3 amino acid residues long.
In another embodiment $X_1$ consists of 2 amino acid residues.

In another embodiment the amino acid residues in $X_1$ are hydrophobic amino acid residues which may be the same or different and are selected from the group consisting of Phe, Leu, Ile, Tyr, Trp, Val, Met and Ala.

In another embodiment the amino acid residues in $X_1$ are selected from the group consisting of Phe, Leu, Ile, Tyr, Trp, Val, Met, Ala, Asp and Gly.

In one embodiment of the invention $X_1$ is Leu-Ala.
In another embodiment of the invention $X_1$ is Phe-Leu.
In another embodiment of the invention $X_1$ is Leu-Gly.
In another embodiment of the invention $X_1$ is Leu-Leu.
In another embodiment of the invention $X_1$ is Leu-Met.
In another embodiment of the invention $X_1$ is Leu-Ile.

In one embodiment of the invention $X_3$ is a Kex2 cleavage site and $X_4$ is peptide bond.

In a further embodiment of the invention $X_3$ is a Kex2 cleavage site, $X_4$ is peptide bond and Z is peptide chain of 2-10 amino acid residues which may be the same or different.

In a further embodiment of the invention $X_3$ is a Kex2 cleavage site, $X_4$ is peptide bond and Z is peptide chain of 2-8 amino acid residues which may be the same or different.

In a further embodiment of the invention $X_3$ is a Kex2 cleavage site, $X_4$ is peptide bond and Z is peptide chain of 3-5 amino acid residues which may be the same or different.

In a further embodiment of the invention $X_1$ comprises 2-5 amino acid residues which may be the same or different and are selected from the group consisting of Phe, Leu, Ile, Tyr, Trp, Val, Met and Ala, $X_3$ is a Kex2 cleavage site, $X_4$ is peptide bond and Z is peptide chain of 3-5 amino acid residues which may be the same or different.

In a further embodiment of the invention $X_1$ comprises 2-5 amino acid residues which may be the same or different and are selected from the group consisting of Phe, Leu, Ile, Tyr, Trp, Val, Met and Ala, $X_3$ is a Kex2 cleavage site, $X_4$ is peptide bond and Z has the sequence D-$X_5$-DLG (SEQ ID NO:4) where $X_5$ is selected from the group consisting of A, R, N, D, N, Q, E, G, H, I, L, K, M, F, P, S, T, W, Y and V.

In a further embodiment of the invention $X_1$ comprises 2-5 amino acid residues which may be the same or different and are selected from the group consisting of Phe, Leu, Ile, Tyr, Trp, Val, Met and Ala, $X_3$ is a Kex2 cleavage site, $X_4$ is peptide bond and Z has the sequence DD$X_6$LG (SEQ ID NO:24) where $X_6$ is selected from the group consisting of A, R, N, D, N, Q, E, G, H, I, L, K, M, F, P, S, T, W, Y and V.

In a further embodiment of the invention $X_1$ consists of 2 amino acid residues which may be the same or different and are selected from the group consisting of Phe, Leu, Ile, Tyr, Trp, Val, Met and Ala, $X_3$ is a Kex2 cleavage site, $X_4$ is peptide bond and Z is peptide chain of 3-5 amino acid residues which may be the same or different.

In a further embodiment of the invention $X_1$ consists of 2 amino acid residues which may be the same or different and are selected from the group consisting of Phe, Leu, Ile, Tyr, Trp, Val, Met and Ala, $X_3$ is a Kex2 cleavage site, $X_4$ is peptide bond and Z has the sequence D-$X_5$-DLG (SEQ ID NO:4) where $X_5$ is selected from the group consisting of A, R, N, D, N, Q, E, G, H, I, L, K, M, F, P, S, T, W, Y and V.

In a further embodiment of the invention $X_1$ consists of 2 amino acid residues which may be the same or different and are selected from the group consisting of Phe, Leu, Ile, Tyr, Trp, Val, Met and Ala, $X_3$ is a Kex2 cleavage site, $X_4$ is peptide bond and Z has the sequence DD$X_6$LG (SEQ ID NO:24) where $X_6$ is selected from the group consisting of A, R, N, D, N, Q, E, G, H, I, L, K, M, F, P, S, T, W, Y and V.

In another embodiment of the invention $X_3$ and Z are peptide bonds and $X_4$ is an aminopeptidase cleavage site. In this embodiment a suitable aminopeptidase cleavage site is EAEA (SEQ ID NO:3).

Z may be of the size from 1, 2, 3, 4, 5, 7, 7, 8, 9, 10, 11, 12, 13, 14, 15, 16, 17, 18, 19, 20, 21, 22, 23, 24, 25, 26, 27, 28, 29, 30 31, 32, 33, 34 and 35 amino acid residues.

In one embodiment Z is of the size 1-35, 1-34, 1-33, 1-31, 1-30, 1-29, 1-28, 1-27, 1-26, 1-25, 1-24, 1-23, 1-22, 1-21, 1-20, 1-19, 1-18, 1-17, 1-16, 1-15, 1-14, 1-13, 1-12, 1-11, 1-10, 1-9, 1-8, 1-7, 1-6, 1-5, 1-4, 1-3 or 1-2 amino acid residues.

In a further embodiment Z is of the size 2-35, 2-34, 2-33, 2-31, 2-30, 2-29, 2-28, 2-27, 2-26, 2-25, 2-24, 2-23, 2-22, 2-21, 2-20, 2-19, 2-18, 2-17, 2-16, 2-15, 2-14, 2-13, 2-12, 2-11, 2-10, 2-9, 2-8, 2-7, 2-6, 2-5, 2-4 or 2-3 amino acid residues.

In a further embodiment Z is of the size 3-35, 3-34, 3-33, 3-31, 3-30, 3-29, 3-28, 3-27, 3-26, 3-25, 3-24, 3-23, 3-22, 3-21, 3-20, 3-19, 3-18, 3-17, 3-16, 3-15, 3-14, 3-13, 3-12, 3-11, 3-10, 3-9, 3-8, 3-7, 3-6, 3-5 or 3-4 amino acid residues.

In a further embodiment Z is of the size 4-35, 4-34, 4-33, 4-31, 4-30, 4-29, 4-28, 4-27, 4-26, 4-25, 4-24, 4-23, 4-22, 4-21, 4-20, 4-19, 4-18, 4-17, 4-16, 4-15, 4-14, 4-13, 4-12, 4-11, 4-10, 4-9, 4-8, 4-7, 4-6 and 4-5 amino acid residues.

In another embodiment Z is of the size 1 to 10 amino acid residues.

In another embodiment Z is of the size 1 to 5 amino acid residues.

In another embodiment Z is of the size 2-10, 2-8, 2-7, 2 to 6, 2-5 or 2-4 amino acid residues.

In another embodiment Z is of the size 3-5 amino acid residues.

In a further embodiment the amino acid residue in the position penultimate to the cleavage site $X_3$ is selected from the group consisting of Leu, Ile, Tyr, Arg, Lys, His, Phe, Met, Val and Pro.

In one embodiment the amino acid residue in Z in the position penultimate to the cleavage site $X_3$ is Leu.

In one embodiment the amino acid residue in Z in the position penultimate to the cleavage site $X_3$ is Ile.

In one embodiment the amino acid residue in Z in the position penultimate to the cleavage site $X_3$ is Tyr.

In one embodiment the amino acid residue in Z in the position penultimate to the cleavage site $X_3$ is Arg.

In one embodiment the amino acid residue in Z in the position penultimate to the cleavage site $X_3$ is Lys.

In one embodiment the amino acid residue in Z in the position penultimate to the cleavage site $X_3$ is His.

In one embodiment the amino acid residue in Z in the position penultimate to the cleavage site $X_3$ is Pro.

In one embodiment the amino acid residue in Z in the position penultimate to the cleavage site $X_3$ is Phe.

In one embodiment the amino acid residue in Z in the position penultimate to the cleavage site $X_3$ is Met.

In one embodiment the amino acid residue in Z in the position penultimate to the cleavage site $X_3$ is Val.

The remaining amino acid residues in Z may be any codable amino acid residue, which may be the same or different. However, in one embodiment the amino acid residue in the position penultimate to the cleavage site $X_3$ is not Asp, Glu, Gly or Ala.

In one embodiment Z has the sequence DLG, DDLG (SEQ ID NO:1) or DDDLG (SEQ ID NO:2).

In another embodiment Z has the sequence DLG.

In one embodiment Z has the sequence D-$X_5$-DLG (SEQ ID NO:4) where $X_5$ is selected from the group consisting of A, R, N, D, N, Q, E, G, H, I, L, K, M, F, P, S, T, W, Y and V.

In a further embodiment $X_5$ is selected from the group consisting of A, R, N, D, Q, H, I, L, P, S, T and Y.

In one embodiment Z has the sequence DDDLG (SEQ ID NO:2).

In one embodiment Z has the sequence DADLG (SEQ ID NO:5).

In another embodiment Z has the sequence DRDLG (SEQ ID NO:6).

In another embodiment Z has the sequence DNDLG (SEQ ID NO:7).

In another embodiment Z has the sequence DQDLG (SEQ ID NO:9).

In another embodiment Z has the sequence DEDLG (SEQ ID NO:10).

In another embodiment Z has the sequence DGDLG (SEQ ID NO:11).

In another embodiment Z has the sequence DHDLG (SEQ ID NO:12).

In another embodiment Z has the sequence DIDLG (SEQ ID NO:13).

In another embodiment Z has the sequence DLDLG (SEQ ID NO:14).

In another embodiment Z has the sequence DKDLG (SEQ ID NO:15).

In another embodiment Z has the sequence DMDLG (SEQ ID NO:16).

In another embodiment Z has the sequence DFDLG (SEQ ID NO:17).

In another embodiment Z has the sequence DPDLG (SEQ ID NO:18).

In another embodiment Z has the sequence DSDLG (SEQ ID NO:19).

In another embodiment Z has the sequence DTDLG (SEQ ID NO:20).

In another embodiment Z has the sequence DWDLG (SEQ ID NO:21).

In another embodiment Z has the sequence DYDLG (SEQ ID NO:22).

In another embodiment Z has the sequence DVDLG (SEQ ID NO:23).

In another embodiment Z has the sequence DD$X_6$LG (SEQ ID NO:24) where $X_6$ is selected from the group consisting of A, R, N, D, N, Q, E, G, H, I, L, K, M, F, P, S, T, W, Y and V.

In another embodiment $X_6$ is selected from the group consisting of R, N, D, N, E, H, K and S.

In one embodiment Z has the sequence DDALG (SEQ ID NO:25).

In another embodiment Z has the sequence DDRLG (SEQ ID NO:26).

In another embodiment Z has the sequence DDNLG (SEQ ID NO:27).

In another embodiment Z has the sequence DDQLG (SEQ ID NO:29).

In another embodiment Z has the sequence DDELG (SEQ ID NO:30).

In another embodiment Z has the sequence DDGLG (SEQ ID NO:31).

In another embodiment Z has the sequence DDHLG (SEQ ID NO:32).

In another embodiment Z has the sequence DDILG (SEQ ID NO:33).

In another embodiment Z has the sequence DDLLG (SEQ ID NO:34).

In another embodiment Z has the sequence DDKLG (SEQ ID NO:35).

In another embodiment Z has the sequence DDMLG (SEQ ID NO:36).

In another embodiment Z has the sequence DDFLG (SEQ ID NO:37).

In another embodiment Z has the sequence DDPLG (SEQ ID NO:38).

In another embodiment Z has the sequence DDSLG (SEQ ID NO:39).

In another embodiment Z has the sequence DDTLG (SEQ ID NO:40).

In another embodiment Z has the sequence DDWLG (SEQ ID NO:41).

In another embodiment Z has the sequence DDYLG (SEQ ID NO:42).

In another embodiment Z has the sequence DDVLG (SEQ ID NO:43).

The target insulin molecule may be an insulin analogue which has been further modified in the A- and/or B-chain as long as such modifications do not have an adverse effect on the insulin activity of the target insulin molecule.

By "insulin analogue" as used herein is meant a polypeptide with insulin activity which has a molecular structure which formally can be derived from the structure of a naturally occurring insulin, for example that of human insulin, by deleting and/or substituting at least one amino acid residue occurring in the natural insulin and/or by adding at least one amino acid residue. The added and/or substituted amino acid residues can either be codable amino acid residues or other naturally occurring amino acid residues or purely synthetic amino acid residues.

The insulin analogues will typically not comprise more than about 7 mutations, more typically not more than 5 and even more typically at the most 3 mutations compared to human insulin.

Over the years a fairly large number of modification of the insulin A- and or B-chain have been disclosed. Thus the position 28 of the B chain may be modified from the natural Pro residue to Asp, Lys, or Ile and Lys in position B29 may also be modified to Pro.

Also, Asn at position A21 may be modified to Ala, Gln, Glu, Gly, His, Ile, Leu, Met, Ser, Thr, Trp, Tyr or Val, in particular to Gly, Ala, Ser, or Thr and in particular to Gly. Furthermore, Asn at position B3 may be modified to Lys or Asp. Further examples of insulin analogues are des(B30) human insulin, insulin analogues wherein one or both of B1 and B2 have been deleted; insulin analogues wherein the A-chain and/or the B-chain have an N-terminal extension and insulin analogues wherein the A-chain and/or the B-chain have a C-terminal extension. Also, the natural amino acid residue in position A18 may be changed to a Gln residue or one or more of the amino acid residue in positions B26-B30 or positions B27-30 have been deleted.

Examples of insulin analogues which can be produced by the present method are $Gly^{A21}$ human insulin, $Gly^{A21}$ des (B30) human insulin, desB1 human insulin, des B30 human insulin, $Asp^{B28}$ human insulin and $Lys^{B28}Pro^{B29}$ human insulin.

Further examples of insulin analogues are human insulin analogues containing mutations in one or more of positions A21, B10, A8, A14, B25, B27 and B1.

The target insulin molecule may also by an insulin molecule wherein the C-terminal extension of the B-chain is not cleaved off in the subsequent cleavage step.

Such insulin analogues will have the structure B-$X_1$ . . . A, where B, A and $X_1$ have the above meanings and where the B- and the A-chain are connected by two disulphide bridges as in human insulin.

The fungi cell may by any fungi cell as all fungi have the necessary proteolytic activity to cleave insulin precursor molecules of the present type to cleave off the connecting peptide and liberate a two chain molecule. However, over the years yeast has proven to be an efficient cell type for expressing and secreting of small peptides of the size of insulin. In particular the yeast *Saccharomyces cerevisiae* has proven to be useful.

Thus in one embodiment of the invention the fungi cell is a yeast cell and in a further embodiment the yeast cell is *Saccharomyces cerevisiae*.

In a further aspect the present invention is related to insulin analogues having a C-terminal extension of the B-chain of human insulin. This extension will have from 1-5 amino acid residues typically selected from the group consisting of Phe, Leu, Ile, Tyr, Trp, Val, Met, Asp, Gly and Ala.

Non limiting examples of insulin analogues having a C-terminal extension are B31 Leu, B32Ala human insulin; B31Leu, B32Ala, desB30 human insulin, B31Phe, B32Leu human insulin and B31Phe, B32Leu, desB30 human insulin.

The human insulin analogues according to the present invention may be used in the treatment of states which are sensitive to insulin. Thus, they can be used in the treatment of type 1 diabetes, type 2 diabetes and hyperglycaemia for example as sometimes seen in seriously injured persons and persons who have undergone major surgery.

In a further aspect the present invention is related to pharmaceutical formulations comprising the human insulin analogues in combination with suitable pharmaceutically acceptable adjuvants and additives such as one or more agents suitable for stabilization, preservation or isotonicity.

BRIEF DESCRIPTION OF THE DRAWINGS

The patent or application file contains at least one drawing executed in color. Copies of this patent or patent application publication with color drawing(s) will be provided by the Office upon request and payment of necessary fee.

FIG. 1 shows an example of a yeast plasmid called ESI42-33. The plasmid contains an expression cassette comprising an EcoRI-XbaI fragment inserted into the plasmid between the transcription-promoter and the transcription-terminator of the *S. cerevisiae* TPI gene;

FIG. 2 shows the NcoI-XbaI DNA fragment (SEQ ID NO:44) encoding the insulin precursor A14E, B25H, B(1-30)-LARRDLGKR (SEQ ID NO:45)-(A1-21) human insulin and the amino acid sequence of the insulin precursor including a short up stream sequence (SEQ ID NO:46);

DETAILED DESCRIPTION OF THE INVENTION

Figure 3:
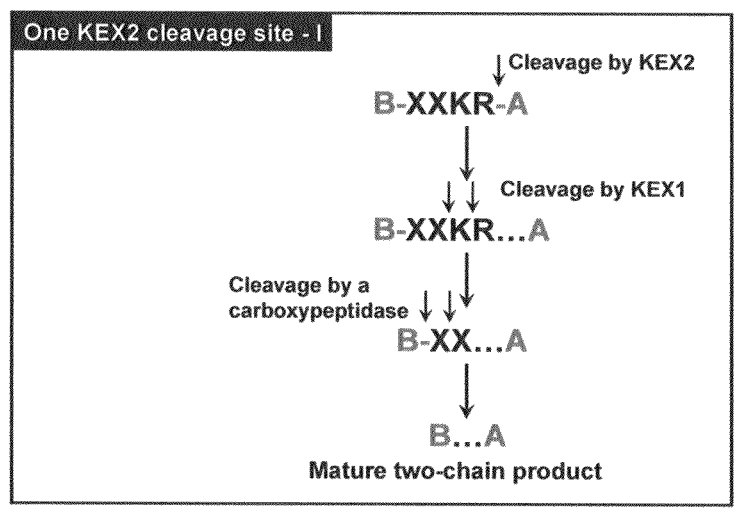
FIG. 3 shows the cleavage sequence of one embodiment of the invention.

Production of insulin by secretion of the mature product directly to the fermentation broth requires intracellular processing of insulin precursors comprising a connecting peptide flanked by a cleavage site at each ends. Such connecting peptide may be of the type B-KR(W)$_n$KR-A where B is the B-chain of human insulin, A is the A-chain of human insulin and W is a peptide chain of varying length. The intracellular processing is facilitated by the Golgi proteases Kex1 and Kex2. In this process two significant problems have been encountered: 1) The ability of Kex2 to digest the Kex2 site linked to the B-chain is strongly influenced by residue 29 and 30 of the B-chain and 2) the product secreted by the cell is a mixture of mature insulin and insulin lacking the B30 threonine. The proteolytic activity responsible for the removal of B30Thr is most likely Kex1. However, the two forms of insulin can not be separated in downstream processes, making it paramount to ensure a more homogeneous product formation.

The modified C-peptide according to the present invention is designed to facilitate an efficient cleavage of the modified C-peptide from the A and B chain of the insulin molecule to form a mature insulin molecule. A new type of C-peptides have been developed, which addresses the problems described above. According to the invention the B-chain is extended at its C-terminal end with a short peptide sequence attached at its other end to the Kex2 site in the C-peptide. Insertion of a short amino acid sequence in this position will allow for optimisation of the N-terminal Kex2 site, making more efficient Kex2 cleavage possible. Complete processing by Kex1 and Kex2 results in a two-chain insulin precursor molecule with an extension of the C-terminal end of the B-chain of the form B-(X)$_n$ . . . A, where X is the C-terminal extension to the B-chain and the A- and the B-chain are connected by the two disulphide bridges.

A vacuolar yeast protease, carboxypeptidase Y (CPY), has been proven to be inefficient in removal of the B30 amino acid residue if this is Thr (the natural amino acid residue in this position in the human insulin molecule). Furthermore, the extra amino acid residues N-terminally of the Kex2p site in the connecting peptide and C-terminal of B30 amino acid residue can be designed to be optimal substrates for CPY ultimately leading to a more homogenous product formation.

The proteolytic step catalysed by CPY can take place in three ways:

1) by addition of CPY directly to the fermentation broth to process the C-terminally extended, two chain product, B-(X)$_n$ . . . A, being secreted by the cell;

2) by processing the C-terminally extended, two chain product, B-(X)$_n$ . . . A, by an endogenous CPY on its way through the secretory pathway or 3) by processing two chain product, B-(X)$_n$ . . . A, by CPY either by overexpression of PRC1, the gene that encodes CPY, or by mutations leading to mislocalization of CPY to the culture media.

In a wild type yeast strain, CPY is localized to the vacuole. The transport of the inactive precursor, proCPY, from the Golgi to the vacuole is mediated by the vacuolar protein sorting machinery. Overexpression of PRC1 leads to saturation of the vacuolar protein sorting, whereby CPY is secreted to the exterior (Stevens et al., J. Cell Biol. 102 (1986), 1551-1557). Secretion to the culture media can also be achieved by certain mutations in genes that encode proteins involved in vacuolar protein sorting (Rothman and Stevens, Cell, 47 (1986), 1041-1051). For instance, a deletion of VPS1 results in efficient secretion of CPY (Nielsen et al, App. Microbiol. Biotech. 33 (1990) 307-312). Also, mutations in the propeptide of CPY result in a secretion phenotype (Valls et al., J. Cell Biol. 111 (1990), 361-368).

The proteolytic step for removal of possible extensions from the N-terminal of the A-chain can be catalyzed by an aminopeptidase. Dipeptidyl aminopeptidases catalyze the sequential removal of dipeptides from the N-terminus of polypeptides. The proteolytic step can, similar to the CPY processing, take place by dipeptidyl aminopeptidases residing inside the cell, secreted to the culture media, or added directly to the fermentation broth. The yeast, Saccharomyces cerevisiae, harbors two endogenous dipeptidyl aminopeptidase, the vacuolar protein Dap2p and the Golgi integral membrane protein Step 13p (Roberts et al., (1989), J. Cell Biol. 108:1363-1373; Julius et al., (1983), Cell 32:839-852). Step 13p cleaves on the carboxyl side of X-Ala- or X-Pro-sequences (where X is an amino acid), and could participate in the processing of insulin precursor molecules traversing through the secretory pathway.

Figure 4:
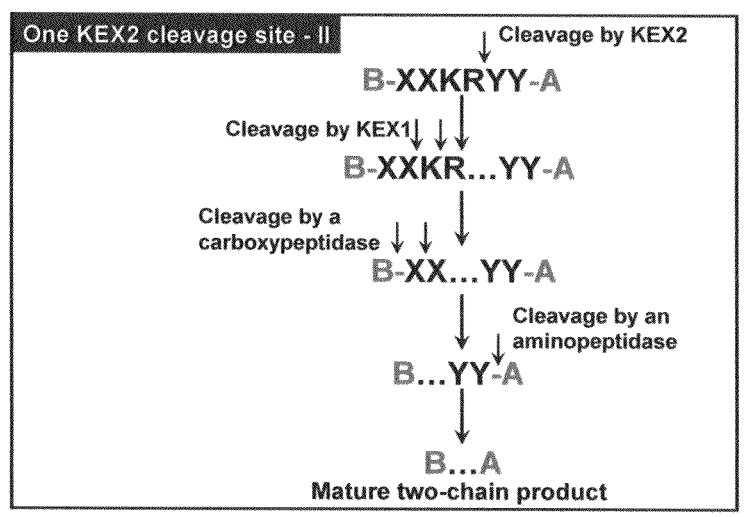
FIG. 4 shows the cleavage sequence of another embodiment of the invention.
Figure 5:
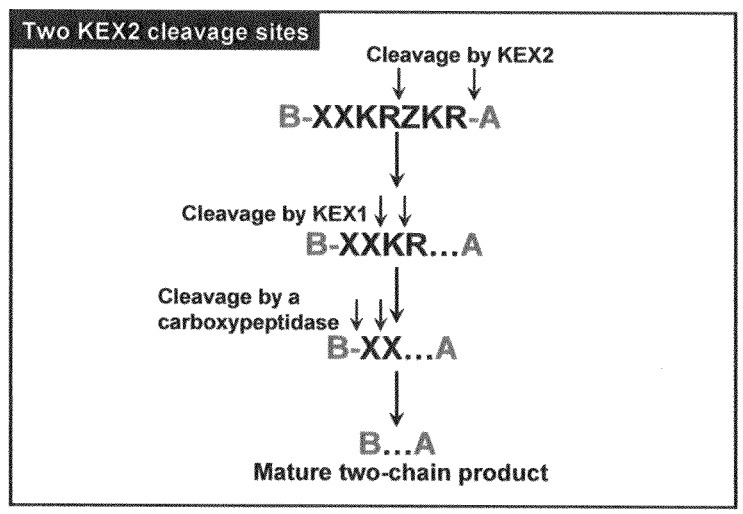
FIG. 5 shows the cleavage sequence of a further embodiment of the invention.

The various processing patterns of the invention are illustrated schematically in FIGS. 3-5.

In FIG. 3 the insulin precursor construct has a single Kex2 site, KR, and a C-terminal extension of the B-chain illustrated by the sequence XX in the connecting peptide. The first cleavage is a cleavage of the Kex2 site by Kex2 to open the single-chain structure to a two-chain structure having the sequence XXKR attached to the B-chain. Then the enzyme Kex1 will cleave off the KR-sequence and finally carboxypeptidase will cleave off the XX-extension of the B-chain to give a mature two-chain insulin product.

In FIG. 4 an alternative embodiment is illustrated. In this embodiment the insulin precursor has a single Kex2 site and an aminopeptidase cleavage site, YY, in the connecting peptide. As in FIG. 3 Kex2, Kex1 and carboxypeptidase will remove the XX-KR sequence. However, in this embodiment a final aminopeptidase cleavage will remove the YY-sequence to give the mature, two-chain insulin product.

In the embodiment illustrated in FIG. 5 the insulin precursor has two Kex2 cleavage sites connected by a peptide chain Z. The first cleavage with Kex2 removes the Z-KR sequence, the Kex1 takes off the KR-sequence and finally carboxypeptidase removes the XX-sequence.

It should be noted that the Kex2 and Kex1 cleavages both take place within the fungi cell whereas the cleavage with carboxypeptidase as explained above may take place either within the fungi cell or in the culture medium. Furthermore, the carboxypeptidase may either by an endogenous enzyme or may be added to the culture medium. The same applies to the aminopeptidase cleavage illustrated in FIG. 4.

The target insulin product of the process may either be a two-chain human insulin or a two-chain human insulin analogue which may or may not have a short C-terminal extension of the B-chain. If the target insulin product has no C-terminal extension of the B-chain, then the C-terminal extension of the B-chain should be capable of subsequently being cleaved off from the B-chain before further purification steps. Depending on the amino acid residue in position B30 the carboxypeptidase may also take off the B30 amino acid residue resulting in a desB30 insulin analogue.

The removal of the C-terminal extension of the B-chain will typically take place by means of a carboxy-peptidase activity. The proteolytic step catalysed by such carboxypeptidase activity can be effected either by addition of the appropriate enzyme directly to the fermentation broth to process C-terminal extension of the B-chain in the precursor molecule secreted by the cell.

The carboxypeptidase may be any suitable natural carboxypeptidase such as CPY or a mutated variant thereof.

Alternatively the extension may be processed by a carboxypeptidase (endogeneous or expressed from a plasmid) of the precursor molecule in the cell on its way through the secretory pathway.

Thus in one embodiment the C-terminal extension of the B-chain is cleaved off within the fungi cell and in another embodiment it is subsequently cleaved of in the culture medium giving rise to the formation of mature human insulin or an analogue thereof.

The C-peptide will typically comprise two Kex2 cleavage sites with a peptide sequence interposed between the two Kex2 sites. The length and the amino acid composition of the peptide sequence between the two Kex2 sites may vary as long as it enables folding of the expressed single-chain insulin precursor and establishing of the correct positioned disulfide bridges in the precursor molecule.

The size of the natural C-peptide is of 35 amino acid residues. Thus in one aspect of the present invention the peptide sequence between the two Kex2 sites will be of about the same length as the natural C-peptide.

Cleavage of the Kex2 site attached to the A-chain may be enhanced if the peptide sequence interposed between the two Kex2 sites comprise a Leu, Ile, Tyr, Arg, Lys, His, Pro, Phe, Met or Val amino acid residue in the position penultimate to the Kex2 site adjacent to the A-chain. We have also discovered that the amino acid residue in the same position should not be Asp, Glu, Gly or Ala.

The production of high amounts of mature insulin or insulin analogue from the fungi cell will significantly reduce the number of down stream purification steps necessary to produce an insulin product of a purity sufficiently high for pharmaceutical purposes. Thus, in the method for making insulin in yeast disclosed in U.S. Pat. No. 4,916,212 an insulin precursor is converted into human insulin in two steps i.e. a transpeptidation to convert the single chain insulin precursor B(1-29)-Alal-Ala-Lys-A(1-21) into an ester of human insulin and then a hydrolysis of the insulin ester into human insulin. Each conversion step will require an initial separation step and at least one subsequent purification step. Thus at least six additional steps are necessary to produce the mature insulin including at least one enzymatic conversion.

It is well known that no enzymatic cleavage runs to a 100% cleavage leaving impurities of uncleaved or partially cleaved impurities which have to be efficiently removed in the case of pharmaceutical products. Thus, each cleavage step will be followed by at least one isolation or purification step, typically a chromatographic purification by means of exchange chromatography, gel filtration chromatography, affinity chromatography, or the like.

Chromatographic column material for use in commercial scale is very expensive and therefore reduction of the number of such chromatographic steps has a significant impact on the production economy. A reduction of the downstream conversion and purification step will in addition reduced the amount of labor work and hours spent in the process and thus further improve the production economy.

In the present process where the mature insulin or an analogue thereof can be isolated in high yields directly from the culture broth much fewer down stream process steps are necessary to produce a product of sufficient purity for pharmaceutical use.

The DNA sequence encoding the insulin precursor may be of genomic or cDNA origin, for instance be obtained by preparing a genomic or cDNA library and screening for DNA sequences coding for all or part of the polypeptide by hybridisation using synthetic oligonucleotide probes in accordance with standard techniques (see, for example, Sambrook, J, Fritsch, E F and Maniatis, T, *Molecular Cloning: A Laboratory Manual*, Cold Spring Harbor Laboratory Press, New York, 1989). The DNA sequence encoding the insulin precursore may also be prepared synthetically by established standard methods, e.g. the phosphoamidite method described by Beaucage and Caruthers, *Tetrahedron Letters* 22 (1981), 1859-1869, or the method described by Matthes et al., *EMBO Journal* 3 (1984), 801-805. The DNA sequence may also be prepared by polymerase chain reaction using specific primers, for instance as described in U.S. Pat. No. 4,683,202 or Saiki et al., *Science* 239 (1988), 487-491.

The DNA sequence may be inserted into any vector which may be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The vector is preferably an expression vector in which the DNA sequence encoding the insulin precursor is operably linked to additional segments required for transcription of the DNA, such as a promoter. The promoter may be any DNA sequence which shows transcriptional activity in the host cell of choice and may be derived from genes encoding proteins either homologous or heterologous to the host cell.

Examples of suitable promoters for use in yeast host cells include promoters from yeast glycolytic genes (Hitzeman et al., J. Biol. Chem. 255 (1980), 12073-12080; Alber and Kawasaki, J. Mol. Appl. Gen. 1 (1982), 419-434) or alcohol dehydrogenase genes (Young et al., in Genetic Engineering of Microorganisms for Chemicals (Hollaender et al, eds.), Plenum Press, New York, 1982), or the TPI1 (U.S. Pat. No. 4,599,311) or ADH2-4-c (Russell et al., Nature 304 (1983), 652-654) promoters.

The DNA sequence encoding the insulin precursor may also, if necessary, be operably connected to a suitable terminator, polyadenylation signals, transcriptional enhancer sequences, and translational enhancer sequences. The recombinant vector of the invention may further comprise a DNA sequence enabling the vector to replicate in the host cell in question.

To direct the insulin into the secretory pathway of the host cells, a secretory signal sequence (also known as a leader sequence, prepro sequence or pre sequence) may be provided in the recombinant vector. The secretory signal sequence is joined to the DNA sequence encoding the insulin precursor in the correct reading frame. Secretory signal sequences are commonly positioned 5' to the DNA sequence encoding the peptide. The signal peptide may be a naturally occurring signal peptide, or a functional part thereof, or it may be a synthetic peptide.

For efficient secretion in yeast, a sequence encoding a leader peptide may also be inserted downstream of the signal sequence and upstream of the DNA sequence encoding the insulin precursor.

The yeast host cell into which the DNA sequence or the recombinant vector is introduced may be any yeast cell which is capable of expressing the insulin precursor and includes *Saccharomyces* spp. or *Schizosaccharomyces* spp., in particular strains of *Saccharomyces cerevisiae* or *Saccharomyces kluyveri*. Further examples of suitable yeast cells are strains of *Kluyveromyces*, such as *K. lactis, Hansenula*, e.g. *H. polymorpha*, or *Pichia*, e.g. *P. pastoris* (cf. Gleeson et al., J. Gen. Microbiol. 132, 1986, pp. 3459-3465; U.S. Pat. No. 4,882, 279).

Methods for transforming yeast cells with heterologous DNA and producing heterologous poly-peptides there from are described, e.g. in U.S. Pat. No. 4,599,311, U.S. Pat. No. 4,931,373, U.S. Pat. Nos. 4,870,008, 5,037,743, and U.S. Pat. No. 4,845,075. Transformed cells are selected by a phenotype determined by a selectable marker, commonly drug resistance or the ability to grow in the absence of a particular nutrient, e.g. leucine. A preferred vector for use in yeast is the POT1 vector disclosed in U.S. Pat. No. 4,931,373.

The process according to the present invention is a so called fermentation process. The fermentation is preferably carried out in aseptic, stirred tanks with supply lines for addition of compressed, sterile gasses consisting of but not limited to air, oxygen and ammonia. A fermentation tank can contain devices/sensors for monitoring pH, temperature, pressure, agitation rate, dissolved oxygen level, liquid content, foam level, feed addition rates and rates of adding acid and base. Furthermore, the fermentation tank can be equipped with optical devises for monitoring levels of cell density, concentrations of metabolites and products regardless of their physio-chemical form. Formation and consumption of volatile compounds are monitored using gas analysis on the gas inlets to and gas outlets from the fermentation tank. All signals of monitored variables can be used for control purposes allowing for the variables to be maintained within predefined ranges or changed continuously according to predefined profile with respect to time. Alternatively, variables are controlled in response to signal changes from other monitored variable.

The desired product produced during the fermentation is present as soluble extracellular material or as intracellular material either in the form of soluble material or as insoluble material including aggregated material. Formation of product is either constitutive or induced and is dependent or independent of microbial growth. The fermentation process is carried out in tanks with a working volume ranging from 100 mL to 200,000 L. A fermentation process can be operated as a batch process, a fed-batch process, a repeated fed-batch process or a continuous process.

The medium used to culture the cells in the fermentation process may be any conventional medium suitable for growing the host cells, such as minimal or complex media containing appropriate supplements. Suitable media are available from commercial suppliers or may be prepared according to published recipes (e.g. in catalogues of the American Type Culture Collection). Thus the medium will contain at least one carbon source, one or several nitrogen sources, essential salts including salts of potassium, sodium, magnesium, phosphate, nitrate and sulphate, trace metals, water soluble vitamins, process aids including but not limited to protease inhibitors, stabilizers, ligands, antifoam agents and inducers. The medium may contain components which are partly precipitated or dispersed in the liquid medium at some operating conditions including sterilisation by heat. The medium can be made up by the mixing of several liquids and gaseous solutions. These solutions can be mixed prior to entering the fermentation tank or they are supplied to the fermentation tank as separate liquid streams added in a predefined ratio. The ratio between different liquid solutions of medium components can vary during the different stages of the fermentation process meaning that the overall composition of the medium may vary during the course of the fermentation.

A suitable fermentation medium may contain between 20 and 60 mM salts of mM $PO_4^{3-}$, between 50 and 70 mM $K^+$, between 20 and 35 mM $SO_4^{2-}$, between 4 and 6 mM $Na^+$, between 6 and 13 mM $Mg^{2+}$, between 0.5 and 1.5 mM $Mn^{2+}$, between 0.02 and 0.04 mM $Cu^{2+}$, between 0.1 and 0.3 mM $Fe^{2+}$, between 0.01 and 0.05 mM $Zn^{2+}$, trace amounts of Co, Mo and Ni added as part of a complex amino acid source, between 1 and 40 g/L of yeast extract, vitamins selected from m-inositol (between 100 and 250 mg/L), Ca-pantothenate (between 2 and 20 mg/L), thiamine, HCl (between 0.5 and 20 mg/L), pyridoxine (between 0.2 and 20 mg/L), niacin nicotinamide (between 2 and 7 mg/L), biotin (between 0.03 and 0.8 mg/L), and choline-dihydrogencitrate (between 0.1 and 0.2 mg/L), a ligand such as citric acid, $H_2O$ (between 0.5 and 7 g/L) and glucose as carbon source (between 50 and 200 g/L). Nitrogen is added continuously as either gaseous $NH_3$ or liquid $NH_4OH$ in an amount of between 400 and 1800 mM. Tap water is used as a natural source of calcium and $Cl^-$.

The peptide produced by the cells may then be recovered from the culture medium by conventional procedures including separating the host cells from the medium by centrifugation or filtration, precipitating the proteinaceous components of the supernatant or filtrate by means of a salt, e.g. ammonium sulphate, purification by a variety of chromatographic procedures, e.g. ion exchange chromatography, gel filtration chromatography, affinity chromatography, or the like, dependent on the type of peptide in question.

After isolation from the culture broth the mature insulin or insulin analogue may be converted into e.g. acylated forms by acylation of in particular the ε-amino group of the B29Lys residue. Methods for acylation of insulins are well known in the art and disclosed in e.g. EP patents 792,290 and 894,095 and in U.S. Pat. Nos. 5,693,609, 5,646,242, 5,922,675, 5,750, 497 and 6,011,007.

Example of acylated insulins are $N^{\epsilon B29}$-tetradecanoyl des (B30) human insulin, $N^{\epsilon B29}$-lithocholoyl-γ-glutamyl des (B30) human insulin, $N^{\epsilon B29}$—($N^{\alpha}$—(HOOC$(CH_2)_{14}$CO)-γ-Glu) des(B30) human insulin or $N^{\epsilon B29}$—($N^{\alpha}$—(HOOC$(CH_2)_{16}$CO)-γ-Glu) des(B30) human insulin.

With "desB30" or "B(1-29)" is meant a natural insulin B chain or an analogue thereof lacking the B30 amino acid residue.

B(1-30) means the natural B chain of human insulin and "A(1-21)" means the natural insulin A chain A18Q human insulin is an insulin analogue having a Gln in position A18 of the human insulin A-chain. B10E, A8H, A14E is an insulin analogue having a Glu in position B10, a His in position A8 and a Glu in position A14, respectively.

With "B1", "A1" etc. is meant the amino acid residue in position 1 in the B chain of insulin (counted from the N-terminal end) and the amino acid residue in position 1 in the A chain of insulin (counted from the N-terminal end), respectively. The amino acid residue in a specific position may also be denoted as e.g. $Phe^{B1}$ which means that the amino acid residue in position B1 is a phenylalanine residue.

With "C-peptide" is meant the peptide sequence linking the A- and B-peptide chains of the insulin molecule together.

With "mature insulin" is meant a two-chain insulin with the correct amino acid residue composition and the same structural conformation as the natural human insulin molecule i.e. with disulfide bridges between $Cys^{A7}$ and $Cys^{B7}$ and between $Cys^{A20}$ and $Cys^{B19}$ and an internal disulfide bridge between $Cys^{A6}$ and $Cys^{A11}$ and with insulin activity. Thus, a mature insulin according to the present invention would be human insulin. An analogue of mature human insulin will comprise one or more mutations in the insulin molecule as explained previously. Thus an a mature insulin analogue may be B28Asp human insulin, desB30 human insulin, A14Glu, B25His human insulin and B31Leu, B32Ala human insulin.

By "insulin derivative" as used herein is meant a naturally occurring insulin or an insulin analogue which has been chemically modified, e.g. by introducing a side chain in one or more positions of the insulin backbone or by oxidizing or reducing groups of the amino acid residues in the insulin or by acylating a free amino group or a hydroxy group.

With "Kex2" or "Kex2p" is meant a subtilisin-like endoprotease that preferentially catalyzes cleavage after a sequence of two basic residues (lysine or arginine) (Rockwell, N C, Krysan, D J, Komiyama, T & Fuller, R S 2002 Precursor Processing by Kex2/Furin Proteases. Chem. Rev. 102: 4525-4548).

With "Kex1" or "Kex1p" is meant a serine carboxypeptidase that preferentially catalyzes removal of C-terminal lysyl and/or arginyl residues (Shilton B H, Thomas D Y, Cygler M 1997 Crystal structure of Kex1deltap, a prohormone-processing carboxypeptidase from Saccharomyces cerevisiae. Biochemistry 36: 9002-9012).

With CPY is meant carboxypeptidase Y a carboxypeptidase that preferentially catalyses removal of hydrophobic or bulky C-terminal amino acid residues such as Phe and Leu (Remington, S. J. & Breddam, K. (1994) Carboxypeptidases C and D. Methods Enzymol. 244, 231-248)

With "correctly processed" is meant an enzymatic cleavage at the desired cleavage point giving the desired product with correct amino acid residue sequence.

"Efficient cleavage" is intended to mean a cleavage of at least 80%, preferably at least 85% and more preferably at least 95%.

"POT" is the Schizosaccharomyces pombe triose phosphate isomerase gene, and "TPI1" is the S. cerevisiae triose phosphate isomerase gene.

By a "leader" is meant an amino acid sequence consisting of a pre-peptide (the signal peptide) and a pro-peptide.

The term "signal peptide" is understood to mean a pre-peptide which is present as an N-terminal sequence on the precursor form of a protein. The function of the signal peptide is to allow the heterologous protein to facilitate translocation into the endoplasmic reticulum. The signal peptide is normally cleaved off in the course of this process. The signal peptide may be heterologous or homologous to the host organism producing the protein.

An effective signal peptide coding region for filamentous fungal host cells is the signal peptide coding region obtained from Aspergillus oryzae TAKA amylase gene, Aspergillus niger neutral amylase gene, the Rhizomucor miehei aspartic proteinase gene, the Humicola lanuginosa cellulase or lipase gene, or the Rhizomucor miehei lipase or protease gene, Aspergillus sp. amylase or glucoamylase, a gene encoding a Rhizomucor miehei lipase or protease. The signal peptide is preferably derived from a gene encoding A. oryzae TAKA amylase, A. niger neutral a-amylase, A. niger acid-stable amylase, or A. niger glucoamylase.

Useful signal peptides for yeast host cells are obtained from the genes for Saccharomyces cerevisiae a-factor and Saccharomyces cerevisiae invertase. A number of signal peptides which may be used with the DNA construct of the invention including yeast aspartic protease 3 (Yps1) signal peptide or any functional analogue (Egel-Mitani et al. (1990) YEAST 6:127-137 and U.S. Pat. No. 5,726,038) and the α-factor signal of the MFα1 gene (Thorner (1981) in The Molecular Biology of the Yeast Saccharomyces cerevisiae, Strathern et al., eds., pp 143-180, Cold Spring Harbor Laboratory, NY and U.S. Pat. No. 4,870,008, the signal peptide of mouse salivary amylase (cf. O. Hagenbuchle et al., Nature 289, 1981, pp. 643-646), a modified carboxypeptidase signal peptide (cf. L. A. Valls et al., Cell 48, 1987, pp. 887-897) and the yeast BAR1 signal peptide (cf. WO 87/02670).

The term "pro-peptide" means a polypeptide sequence whose function is to allow the expressed polypeptide to be directed from the endoplasmic reticulum to the Golgi apparatus and further to a secretory vesicle for secretion into the culture medium (i.e. exportation of the polypeptide across the cell wall or at least through the cellular membrane into the periplasmic space of the yeast cell). The pro-peptide may be the yeast α-factor pro-peptide, vide U.S. Pat. Nos. 4,546,082 and 4,870,008. Alternatively, the pro-peptide may be a synthetic pro-peptide, which is to say a pro-peptide not found in nature. Suitable synthetic pro-peptides are those disclosed in U.S. Pat. Nos. 5,395,922; 5,795,746; 5,162,498. WO 89/02463, WO 92/11378 and WO 98/32867.

The polynucleotide sequence of the invention may also be of mixed genomic, cDNA, and synthetic origin. For example, a genomic or cDNA sequence encoding a leader peptide may be joined to a genomic or cDNA sequence encoding the A and B chains, after which the DNA sequence may be modified at a site by inserting synthetic oligonucleotides encoding the desired amino acid sequence for homologous recombination in accordance with well-known procedures or preferably generating the desired sequence by PCR using suitable oligonucleotides.

The invention encompasses a vector which is capable of replicating in the selected microorganism or host cell and which carries a polynucleotide sequence encoding the desired insulin product. The recombinant vector may be an autonomously replicating vector, i.e., a vector which exists as an extra-chromosomal entity, the replication of which is independent of chromosomal replication, e.g., a plasmid, an extra-chromosomal element, a mini-chromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used. The vector may be linear or closed circular plasmids and will preferably contain an element(s) that permits stable integration of the vector into the host cell's genome or autonomous replication of the vector in the cell independent of the genome.

In one embodiment, the recombinant expression vector is capable of replicating in yeast. Examples of sequences which enable the vector to replicate in yeast are the yeast plasmid 2 µm replication genes REP 1-3 and origin of replication.

The vector may also comprise a selectable marker, e.g. a gene the product of which complements a defect in the host cell or one which confers resistance to a drug, e.g. ampicillin, kanamycin, tetracyclin, chloramphenicol, neomycin, hygromycin or methotrexate.

Selectable markers for use in a filamentous fungal host cell include amdS (acetamidase), argB (ornithine carbamoyl-transferase), pyrG (orotidine-5'-phosphate decarboxylase) and trpC (anthranilate synthase.

Suitable markers for yeast host cells are ADE2, HIS3, LEU2, LYS2, MET3, TRP1, and URA3. A preferred selectable marker for yeast is the Schizosaccharomyces pompe TPI gene (Russell (1985) Gene 40:125-130).

In the vector, the polynucleotide sequence is operably connected to a suitable promoter sequence. The promoter may be any nucleic acid sequence which shows transcriptional activity in the host cell of choice including mutant, truncated, and hybrid promoters, and may be obtained from genes encoding extra-cellular or intra-cellular polypeptides either homologous or heterologous to the host cell.

Examples of suitable promoters for directing the transcription in a filamentous fungal host cell are promoters obtained from the genes for *Aspergillus oryzae* TAKA amylase, *Rhizomucor miehei* aspartic proteinase, *Aspergillus niger* neutral alpha-amylase, and *Aspergillus niger* acid stable alpha-amylase.

In a yeast host, useful promoters are the *Saccharomyces cerevisiae* MFα1, TPI, ADH or PGK promoters.

The polynucleotide construct of the invention will also typically be operably connected to a suitable terminator. In yeast a suitable terminator is the TPI terminator (Alber et al. (1982) J. Mol. Appl. Genet. 1:419-434).

The procedures used to ligate the DNA sequences coding for the insulin product, the promoter and optionally the terminator and/or secretory signal sequence, respectively, and to insert them into suitable vectors containing the information necessary for replication, are well known to persons skilled in the art (cf., for instance, Sambrook et al., Molecular Cloning: A Laboratory Manual, Cold Spring Harbor, N.Y., 1989).

It will be understood that the vector may be constructed either by first preparing a DNA construct containing the entire DNA sequence encoding the insulin precursors of the invention, and subsequently inserting this fragment into a suitable expression vector, or by sequentially inserting DNA fragments containing genetic information for the individual elements (such as the signal, pro-peptide, modified C-peptide, A and B chains) followed by ligation.

The present invention also relates to recombinant fungi cells, comprising a polynucleotide sequence encoding the desired insulin product. A vector comprising such polynucleotide sequence is introduced into the host cell so that the vector is maintained as a chromosomal integrant or as a self-replicating extra-chromosomal vector as described earlier. The term "host cell" encompasses any progeny of a parent cell that is not identical to the parent cell due to mutations that occur during replication.

The host cell used in the present invention is a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In one embodiment the fungal host cell is a yeast cell. "Yeast" as used herein includes ascosporogenous yeast (Endomycetales), basidiosporogenous yeast, and yeast belonging to the Fungi Imperfecti (Blastomycetes). The ascosporogenous yeasts are divided into the families Spermophthoraceae and Saccharomycetaceae. The latter is comprised of four subfamilies, Schizosaccharomycoideae (e.g., genus *Schizosaccharomyces*), Nadsonioideae, Lipomycoideae, and Saccharomycoideae (e.g., genera *Pichia, Kluyveromyces* and *Saccharomyces*). The basidiosporogenous yeasts include the genera *Leucosporidim, Rhodosporidium, Sporidiobolus, Filobasidium,* and *Filobasidiella*. Yeast belonging to the Fungi Imperfecti are divided into two families, Sporobolomycetaceae (e.g., genera *Sorobolomyces* and *Bullera*) and Cryptococcaceae (e.g., genus *Candida*). Since the classification of yeast may change in the future, for the purposes of this invention, yeast shall be defined as described in *Biology and Activities of Yeast* (Skinner, F. A., Passmore, S. M., and Davenport, R. R., eds, Soc. App. Bacteriol. Symposium Series No. 9, 1980. The biology of yeast and manipulation of yeast genetics are well known in the art (see, e.g., *Biochemistry and Genetics of Yeast*, Bacil, M., Horecker, B. J., and Stopani, A. O. M., editors, 2nd edition, 1987; *The Yeasts*, Rose, A. H., and Harrison, J. S., editors, 2nd edition, 1987; and *The Molecular Biology of the Yeast Saccharomyces*, Strathern et al., editors, 1981).

The yeast host cell may be selected from a cell of a species of *Candida, Kluyveromyces, Saccharomyces, Schizosaccharomyces, Pichia, Hansenula, Yarrowia*. In one embodiment, the yeast host cell is a *Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis, Schizosaccharomyces pombe, Sacchoromyces uvarum, Pichia kluyveri, Yarrowia lipolytica, Candida utilis, Candida cacaoi,* and *Geotrichum fermentans*. Other useful yeast host cells are a *Kluyveromyces lactis, Kluyveromyces fragilis, Hansenula polymorpha, Pichia pastoris Yarrowia lipolytica, Schizosaccharomyces pombe, Ustilgo maylis, Candida maltose, Pichia guillermondii* and *Pichia methanoliol* (cf. Gleeson et al., *J. Gen. Microbiol.* 132, 1986, pp. 3459-3465; U.S. Pat. No. 4,882,279 and U.S. Pat. No. 4,879,231).

In one embodiment the fungal host cell is a filamentous fungal cell. "Filamentous fungi" include all filamentous forms of the subdivision Eumycota and Oomycota (as defined by Hawksworth et al., 1995, supra). The filamentous fungi are characterized by a vegetative mycelium composed of chitin, cellulose, glucan, chitosan, mannan, and other complex polysaccharides. The filamentous fungal host cell may be chosen from the group consisting of *Acremonium, Aspergillus, Fusarium, Humicola, Mucor, Myceliophthora, Neurospora, Penicillium, Thielavia, Tolypocladium,* and *Trichoderma*

The expression "a codable amino acid" or "a codable amino acid residue" is used to indicate an amino acid or amino acid residue which can be coded for by a triplet ("codon") of nucleotides.

In the present context the three-letter or one-letter indications of the amino acids have been used in their conventional meaning as indicated in the following table. Unless indicated explicitly, the amino acids mentioned herein are L-amino acids. Further, the left and right ends of an amino acid sequence of a peptide are, respectively, the N- and C-termini unless otherwise specified.

Abbreviations for Amino Acids:

| Amino acid | Tree-letter code | One-letter code |
|---|---|---|
| Glycine | Gly | G |
| Proline | Pro | P |
| Alanine | Ala | A |
| Valine | Val | V |
| Leucine | Leu | L |
| Isoleucine | Ile | I |
| Methionine | Met | M |
| Cysteine | Cys | C |
| Phenylalanine | Phe | F |
| Tyrosine | Tyr | Y |
| Tryptophan | Trp | W |
| Histidine | His | H |
| Lysine | Lys | K |
| Arginine | Arg | R |
| Glutamine | Gln | Q |
| Asparagine | Asn | N |

| Amino acid | Tree-letter code | One-letter code |
| --- | --- | --- |
| Glutamic Acid | Glu | E |
| Aspartic Acid | Asp | D |
| Serine | Ser | S |
| Threonine | Thr | T |

By fermentation is meant an aseptic process used for propagating micro-organisms submerged into a liquid medium. The fermentation is preferably carried out in aseptic, stirred tanks with supply lines for addition of compressed, sterile gasses consisting of but not limited to air, oxygen and ammonia. A fermentation tank can contain devices/sensors for monitoring pH, temperature, pressure, agitation rate, dissolved oxygen level, liquid content, foam level, feed addition rates and rates of adding acid and base. Furthermore, the fermentation tank can be equipped with optical devises for monitoring levels of cell density, concentrations of metabolites and products regardless of their physio-chemical form. Formation and consumption of volatile compounds are monitored using gas analysis on the gas inlets to and gas outlets from the fermentation tank. All signals of monitored variables can be used for control purposes allowing for the variables to be maintained within predefined ranges or changed continuously according to predefined profile with respect to time. Alternatively, variables are controlled in response to signal changes from other monitored variable.

The desired product produced during the fermentation is present as soluble extracellular material or as intracellular material either in the form of soluble material or as insoluble material including aggregated material. Formation of product is either constitutive or induced and is dependent or independent of microbial growth. The fermentation process is carried out in tanks with a working volume ranging from 100 mL to 200,000 L. A fermentation process can be operated as a batch process, a fed-batch process, a repeated fed-batch process or a continuous process.

With a batch process is meant a fermentation in which the sterile medium is contained within the fermentation tank before the micro-organisms are added to the tank. During the process acid, base, antifoam agent, inhibitors, stabilizers and inducers are added either automatically or manually. Acid and base are added either as liquid solutions or as gaseous components. These components can be added via one feed line or they can be supplied to the fermentation tank in separate lines. The fermentation tank content is only removed for purposes of analysis during the fermentation process. The entire content of the fermentation tank is harvested at the end of the fermentation process. However, for consecutive batch processes the content of the fermentation tank is only partly harvested and the fermentation tank is refilled with fresh, sterile medium allowing for another batch fermentation to take place.

A fed-batch process is a fermentation in which only a part of the medium is filled into the fermentation tank before the micro-organisms are added. The remaining medium components or remaining amounts of already partly added medium components are supplied to the fermentation tank either as one pulse, as a series of discrete pulses or as a continuous flow added at constant or variable rate. A fed-batch process can be preceded by a batch process followed by the fed-batch operational mode. Medium components added to the fermentation tank during the process consist of but are not limited to growth limiting components, sparingly soluble components, volatile components or components with limited stability in liquid environment. The growth rate of the micro-organisms can be controlled through adjustments of the rate by which medium components are added to the fermentation tank. Acid, base, antifoam, inhibitors, stabilizers and inducer are added during the process either automatically or manually. Acid and base are added either as part of liquid solutions or as gaseous components. All components added during the fed-batch process are supplied via one feed line or they can be supplied to the fermentation tank in separate supply lines. During a fed-batch process the fermentation tank content is only removed for the purposes of analysis. The entire content of the fermentation tank is harvested at the end of the process.

A variant of the fed-batch process is the Repeated-Fed-batch process. A repeated-fed-batch fermentation is carried out similar to a fed-batch process but part of the fermentation tank content is removed at one or several instances during the process. Partial removal of fermentation tank content can be followed by addition of fresh medium. Addition of fresh medium can be followed by a batch process before resuming fed-batch process operation. The composition of fresh medium and the medium added during the fed-batch process are not necessarily identical.

By a continuous process is meant a fermentation in which some of the medium is added to the tank before the micro-organisms are added and the fermentation started. Fresh medium containing all medium components necessary for growth together with inhibitors, inducers, antifoam, acid, base and components stabilizing the product are added continuously. These components can be added via one feed line or they can be supplied to the fermentation tank in separate supply lines in order to increase the stability of the used medium or improve its quality. Acid and base are added either as part of liquid solutions or as gaseous components. All components are added to the fermentation tank as a series of discrete pulses or as a continuous flow added at constant or variable rate. Harvest of the fermentation tank content is carried out continuously in order to maintain the content of the fermentation tank within a predefined range. Growth of the micro-organism can be controlled by the rate of medium addition to the fermentation tank as well as by adjustment of the fermentation tank content.

By a medium is meant a liquid solution containing at least one carbon source, one or several nitrogen sources, essential salts including salts of potassium, sodium, magnesium, phosphate, nitrate and sulphate, trace metals, water soluble vitamins, process aids including but not limited to protease inhibitors, stabilizers, ligands, antifoam agents and inducers. The medium may contain components which are partly precipitated or dispersed in the liquid medium at some operating conditions including sterilisation by heat. The medium can be made up by the mixing of several liquids and gaseous solutions. These solutions can be mixed prior to entering the fermentation tank or they are supplied to the fermentation tank as separate liquid streams added in a predefined ratio. The ratio between different liquid solutions of medium components can vary during the different stages of the fermentation process meaning that the overall composition of the medium may vary during the course of the fermentation. The table below contains a list of concentration ranges for different medium components. These concentrations are calculated as the total amount of an added medium component divided by the initial volume of medium in the fermentation tank. Media concentrations for continuous cultivations are included as the concentrations in medium entering the fermentation tank.

The following table is a review of the typical components of a fermentation medium.

Typical Components of a Fermentation Medium

| Main purpose | Component | Low level | | High level | |
|---|---|---|---|---|---|
| C-sources | Glucose | 0 | | 500 | g/L |
| | Sucrose | 0 | | 500 | g/L |
| | Maltose | 0 | | 500 | g/L |
| | Lactose | 0 | | 300 | g/L |
| | L-Malic acid | 0 | | 200 | g/L |
| | Maltodextrins | 0 | | 600 | g/L |
| | Ethanol | 0 | | 500 | g/L |
| | Methanol | 0 | | 500 | g/L |
| | Pectins | 0 | | 40 | g/L |
| | Fatty acids | 0 | | 50 | g/L |
| | PIT emulsions of oils | 0 | | 20 | g/L |
| | Triglycerides | 0 | | 60 | g/L |
| Inorganic P-source | Salts of orthophosphate | 4 | mM | 100 | mM |
| Minerals essential | Salts of sulphate | 1 | mM | 60 | mM |
| for growth | Salts of ammonium | 0 | | 1800 | mM |
| | Salts of magnesium | 0.5 | mM | 20 | mM |
| | Salts of potassium | 3 | mM | 100 | mM |
| | Salts of sodium | 0.2 | | 500 | mM |
| | Salts of calcium | 1 | mM | 50 | mM |
| Other N-sources | Ammonia | 0 | | 1800 | mM |
| | Urea | 0 | | 900 | mM |
| | Amino acids | 0 | | 25 | g/L |
| | Corn steep liquor | 0 | | 100 | g/L |
| | Yeast extract | 0 | | 75 | g/L |
| | Plant proteins | 0 | | 50 | g/L |
| | Hydrolyzed plant proteins | 0 | | 30 | g/L |
| Trace metals | Fe | 10 | | 350 | µM |
| | Zn | 10 | | 300 | µM |
| | Mn | 5 | | 1500 | µM |
| | Cu | 3 | | 75 | µM |
| | Mo | 0 | | 1 | µM |
| | $H_3BO_3$ | 0 | | 60 | µM |
| Vitamins | Biotin | 0.01 | mg/L | 10 | mg/L |
| | Pantothenate, Ca | 1 | mg/L | 1000 | mg/L |
| | Niacin | 1 | mg/L | 200 | mg/L |
| | Thiamin, HCl | 0.2 | mg/L | 200 | mg/L |
| | p-Aminobenzoic acid | 0 | | 100 | mg/L |
| | Choline dihydrogen citrate | 10 | mg/L | 200 | mg/L |
| | m-Inositol | 10 | mg/L | 2000 | mg/L |
| | Pyridoxine, HCl | 0.2 | mg/L | 100 | mg/L |
| | Folic acid | 0 | | 50 | µg/L |
| | Riboflavin | 0 | | 200 | mg/L |
| | Ascorbic acid | 0 | | 1000 | mg/L |
| Auxotrophy | Uridine/Uracil | 0 | | 1000 | mg/L |
| Process aids and | PPO | 0 | | 1000 | ppm |
| ligands. | PPO-PEO block copolymer | 0 | | 5000 | ppm |
| | Antifoam (silicone based) | 0 | | 1000 | ppm |
| | Antifoam (oil based) | 0 | | 1000 | ppm |
| | Citric acid | 0 | | 1000 | mg/L |
| | Trimethylglycin | 0 | | 10.000 | mg/L |
| | Imidazol | 0 | | 10 | mM |
| | EDTA | 0 | | 100 | µM |
| | L-histidin | 0 | | 1000 | mg/L |
| | Non-metabolizale analogous of carbon sources. | 0 | | 200 | mg/L |

Pharmaceutical compositions containing the insulin analogues of this invention can be used in the treatment of states which are sensitive to insulin. Thus, they can be used in the treatment of type 1 diabetes, type 2 diabetes and hyperglycaemia for example as sometimes seen in seriously injured persons and persons who have undergone major surgery. The optimal dose level for any patient will depend on a variety of factors including the efficacy of the specific insulin analogue employed, the age, body weight, physical activity, and diet of the patient, on a possible combination with other drugs, and on the severity of the state to be treated. It is recommended that the daily dosage of the insulin derivative of this invention be determined for each individual patient by those skilled in the art in a similar way as for known insulin compositions.

Pharmaceutical compositions of the insulin analogues will contain usual adjuvants and additives and are preferably formulated as an aqueous solution. The aqueous medium is made isotonic, for example, with sodium chloride, sodium acetate or glycerol. Furthermore, the aqueous medium may contain zinc ions, buffers and preservatives. The pH value of the composition is adjusted to the desired value and may be between about 4 to about 8.5.

The pharmaceutical composition will comprise usual adjuvants such one or more agents suitable for stabilization, preservation or isotonicity, for example, zinc ions, phenol, cresol, a parabene, sodium chloride, glycerol or mannitol.

The buffer used in the pharmaceutical may be selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid or mixtures thereof.

The pharmaceutically acceptable preservative may be selected from the group consisting of phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, bronopol, benzoic acid, imidurea, chlorohexidine, sodium dehydroacetate, chlorocresol, ethyl p-hydroxybenzoate, benzethonium chloride, chlorphenesine (3p-chlorphenoxypropane-1,2-diol) or mixtures thereof. In a further embodiment of the invention the preservative is present in a concentration from 0.1 mg/ml to 20 mg/ml. In a further embodiment of the invention the preservative is present in a concentration from 0.1 mg/ml to 5 mg/ml. In a further embodiment of the invention the preservative is present in a concentration from 5 mg/ml to 10 mg/ml. In a further embodiment of the invention the preservative is present in a concentration from 10 mg/ml to 20 mg/ml. Each one of these specific preservatives constitutes an alternative embodiment of the invention. The use of a preservative in pharmaceutical compositions is well-known to the skilled person. For convenience reference is made to Remington: The Science and Practice of Pharmacy, 19th edition, 1995.

The isotonicity agent may be selected from the group consisting of a salt (e.g. sodium chloride), a sugar or sugar alcohol, an amino acid (e.g. L-glycine, L-histidine, arginine, lysine, isoleucine, aspartic acid, tryptophan, threonine), an alditol (e.g. glycerol (glycerine), 1,2-propanediol (propyleneglycol), 1,3-propanediol, 1,3-butanediol) polyethyleneglycol (e.g. PEG400), or mixtures thereof. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, soluble starch, hydroxyethyl starch and carboxymethylcellulose-Na may be used. In one embodiment the sugar additive is sucrose. Sugar alcohol is defined as a C4-C8 hydrocarbon having at least one —OH group and includes, for example, mannitol, sorbitol, inositol, galactitol, dulcitol, xylitol, and arabitol. In one embodiment the sugar alcohol additive is mannitol. The sugars or sugar alcohols mentioned above may be used individually or in combination. There is no fixed limit to the amount used, as long as the sugar or sugar alcohol is soluble in the liquid preparation and does not adversely effect the stabilizing effects achieved using the methods of the invention. In one embodiment, the sugar or sugar alcohol concentration is between about 1 mg/ml and about 150 mg/ml. In a further embodiment of the invention the isotonic agent is present in a concentration from 1 mg/ml to 50 mg/ml. In a further embodiment of the invention the isotonic agent is present in a concentration from 1 mg/ml to 7 mg/ml. In a further embodiment of the invention the isotonic agent is present in a concentration from 8 mg/ml to 24 mg/ml. In a further embodiment of the invention the isotonic agent is present in a concentration from 25 mg/ml to 50 mg/ml. The use of an isotonic agent in pharmaceutical compositions is well-known to the skilled person. For convenience reference is made to Remington: The Science and Practice of Pharmacy, 19th edition, 1995.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law). All headings and sub-headings are used herein for convenience only and should not be construed as limiting the invention in any way. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention. The citation and incorporation of patent documents herein is done for convenience only and does not reflect any view of the validity, patentability, and/or enforceability of such patent documents. This invention includes all modifications and equivalents of the subject matter recited in the claims appended hereto as permitted by applicable law.

EXAMPLES

General Procedures

All expressions plasmids are of the C-POT type, similar to those described in EP 171, 142. These are 2μ-based expression vectors characterized by containing the *Schizosaccharomyces pombe* triose phosphate isomerase gene (POT) for the purpose of plasmid selection and stabilization in *S. cerevisiae*. The plasmids also contain the *S. cerevisiae* triose phosphate isomerase promoter and terminator (FIG. 1). These sequences are similar to the corresponding sequences in plasmid pKFN1003 (described in WO 9010075) as are all sequences except the following: 1) the sequence of the EcoRI-XbaI fragment encoding the fusion protein of the leader and the insulin product and 2) a silent mutation has been introduced resulting in removal of a NcoI-site in the 2μ-region in the expression vector. In order to facilitate cloning of different fusion proteins the DNA sequence encoding the MFα1 pre-pro leader has been changed to incorporate a NcoI site (see FIG. 2) and is called the MFα1* pre-pro leader. Thus the NcoI-XbaI fragment is simply replaced by an NcoI-XbaI fragment encoding the insulin construct of interest. Such NcoI-XbaI fragments may be synthesized using synthetic oligonucleotides and PCR according to standard techniques. In addition to the alpha-leader other leaders can be used.

Yeast transformants were prepared by transformation of the host strains *S. cerevisiae* strain MT663 or ME1719. The yeast strain MT663 (MATa/MATα pep-4-3/pep-4-3 HIS4/his4 Δtpi::LEU2/Δtpi::LEU2 Cir') was deposited in the Deutsche Sammlung von Mikroorganismen und Zellkulturen in connection with filing WO 92111378 and was given the deposit number DSM 6278. *S. cerevisiae* strain ME1719 (MATa/α leu2/leu2 pep-4-3/pep-4-3 Δtpi::LEU2/Δtpi::LEU2 Δura3/Δura3 Δyps1::URA3/Δyps1::ura3 Cir+) is described in WO 98/01535.

MT663 or ME1719 were grown on YPGaL (1% Bacto yeast extract, 2% Bacto peptone, 2% galactose, 1% lactate) to an O.D. at 600 nm of 0.6. 100 ml of culture was harvested by centrifugation, washed with 10 ml of water, recentrifuged and resuspended in 10 ml of a solution containing 1.2 M sorbitol, 25 mM Na$_2$EDTA pH=8.0 and 6.7 mg/ml dithiotreitol. The suspension was incubated at 30° C. for 15 minutes, centrifuged and the cells resuspended in 10 ml of a solution containing 1.2 M sorbitol, 10 mM Na2EDTA. 0.1 M sodium citrate, pH 0 5.8, and 2 mg NovozymC3234. The suspension was incubated at 30° C. for 30 minutes, the cells collected by centrifugation, washed in 10 ml of 1.2 M sorbitol and 10 ml of CAS (1.2 M sorbitol, 10 mM CaCl$_2$, 10 mM Tris HCl (Tris=Tris(hydroxymethyl)-aminomethane) pH=7.5) and resuspended in 2 ml of CAS. For transformation, 1 ml of CAS-suspended cells was mixed with approx. 0.1 mg of plasmid DNA and left at room temperature for 15 minutes. 1 ml of (20% polyethylene glycol 4000, 10 mM $CaCl_2$, 10 mM Tris HCl, pH=7.5) was added and the mixture left for a further 30 minutes at room temperature. The mixture was centrifuged and the pellet resuspended in 0.1 ml of SOS (1.2 M sorbitol, 33% v/v YPD, 6.7 mM $CaCl_2$) and incubated at 30° C. for 2 hours. The suspension was then centrifuged and the pellet resuspended in 0.5 ml of 1.2 M sorbitol. Then, 6 ml of top agar (the SC medium of Sherman et al. (1982) Methods in Yeast Genetics, Cold Spring Harbor Laboratory) containing 1.2 M sorbitol plus 2.5% agar) at 52° C. was added and the suspension poured on top of plates containing the same agar-solidified, sorbitol containing medium.

Example 1

Construction of a Yeast Expression System for the Insulin Precursor A14E, B25H, B(1-30)-LARRDLGKR (SEQ ID NO:45)-A(1-21)

FIG. 1 shows a yeast plasmid called pESI42-33. The plasmid contains an expression cassette comprising an EcoRI-XbaI fragment inserted into the plasmid between the transcription-promoter and the transcription-terminator of the S. cerevisiae TPI gene. In plasmid pESI42-33 the EcoRI-XbaI fragment encodes a fusion product composed of the MFα1* pre-pro leader, a Lys-Arg cleavage site for the dibasic processing endopeptidase Kex2, and the insulin precursor A14E, B25H, B(1-30)-LARRDLGKR (SEQ ID NO:45)-A(1-21).

A DNA fragment containing sequences encoding the insulin precursor A14E, B25H, B(1-30)-LARRDLGKR (SEQ ID NO:45)-A(1-21) was constructed using synthetic oligonucleotides and standard PCR amplifications. The resulting PCR fragment was purified, digested with NcoI and XbaI and ligated to the NcoI-XbaI vector fragment of the modified cPOT type expression vector (FIG. 1). The expression plasmid was propagated in E. coli, grown in the presence of ampicillin and isolated using standard techniques (Sambrook et al., 1989). The plasmid DNA was checked for insert by appropriate restriction nucleases (e.g. EcoRI, NcoI, XbaI) and was shown by sequence analysis to contain the proper sequence of the insulin precursor A14E, B25H, B(1-30)-LARRDLGKR (SEQ ID NO:45)-A(1-21). FIG. 2 shows the DNA sequence of an NcoI-XbaI fragment and the corresponding amino acid sequence which corresponds to SEQ ID NO: 46. The plasmid was transformed into S. cerevisiae strain MT663. Yeast transformants harbouring the plasmid were selected by glucose utilization as carbon source on YPD (1% yeast extract, 2% peptone, 2% glucose) agar (2%) plates.

Example 2

Processing of the Insulin Precursor by Addition of CPY Directly to the Fermentation Broth The S. Cerevisiae strain MT663 transformed with a plasmid for expression of A14E, B25H, B(1-30)-LARRDLGKR (SEQ ID NO:45)-A(1-21), was inoculated into 5 ml of a medium consisting of 5 g/L $(NH_4)_2SO_4$, 184 mg/L $(NH_4)_2HPO_4$, 2.88 g/L $KH_2PO_4$, 1.42 g/L $MgSO_4.7H_2O$, 1.28 g/L, $K_2SO_4$, 10.00 g/L succinic acid, 10.00 g/L casamino acids, 0.0112 g/L $FeSO_4.7H_2O$, 0.0086 g/L $MnSO_4.H_2O$, 0.0014 g/L $CuSO_4.5H_2O$, 0.00185 g/L $ZnSO_4.7H_2O$, 0.0129 g/L $CaCl_2.2H_2O$, 0.071 g/L citric acid, 28.0 mg/L m-inositol, 14.0 mg/L choline chloride, 2.8 mg/L thiamine, 2.8 mg/L niacinamide, 2.1 mg/L Ca-pantothenic acid, 0.14 mg/L biotin, 0.14 mg/L folic acid, 40 g/L glucose. The cultivation was carried out at 30° C. for 3 days. LC-MS analysis of the fermentation broth suggested that ~50% of the total secreted insulin species were fully processed (Mw=5763). The remaining ~50% were insulin with the C-terminal of the B-chain extended with LA (Mw=5947). For proteolytic removal of the LA-extension, 100 μl fermentation broth was added 0.8 μl CPY purified from S. cerevisiae (~0.1 Unit), and incubated for 5 minutes, 30° C. before LC-MS analysis. This showed that the LA-extension was completely removed.

Example 3

Additional insulin analogues were prepared as described in example 1. The expression yields were compared with the expression yield of the insulin precursor disclosed in EP patent No. 163529: B(1-29)-Ala-Ala-Lys-A(1-21) (MT748). Furthermore the percent of fully processing by Kex2 measured and compared with an insulin with no C-terminal extension of the B-chain. All insulin analogues have the A14E and B25H mutation.

The results appear from the following table.

| $X_1$ | $X_2$ | Z | $X_3$ | $X_4$ | Yield (in percent relative to MT748) | % fully processed by KEX2 |
|---|---|---|---|---|---|---|
| None | KR | DLG | KR | bond | 190 | 50 |
| LG | KR | DLG | KR | bond | 190 | >90 |
| LA | RR | DLG | KR | bond | 170 | >90 |
| LL | RR | DLG | KR | bond | 146 | >90 |
| LM | RR | DLG | KR | bond | 151 | >90 |
| LI | RR | DLG | KR | bond | 120 | >90 |
| LN | KR | DGL | KR | bond | 175 | >90 |
| LD | KR | DGL | KR | Bond | 200 | >90 |
| LE | KR | DGL | KR | Bond | 190 | >90 |
| LT | KR | DGL | KR | Bond | 200 | >90 |
| LS | KR | DGL | KR | Bond | 170 | >90 |
| LP | KR | DGL | KR | bond | 170 | >90 |

Example 4

Processing of the Insulin Precursor with a Single Kex2 Site by Addition of CPY and DAP1 Directly to the Fermentation Broth The S. cerevisiae strain MT663 transformed with a plasmid for expression of A14E, B25H, B(1-30)-LGRREAEA (SEQ ID NO:47)-(A1-21) was inoculated into 5 ml of a medium similar to that described in example 2.

The cultivation was carried out at 30° C. for 3 days. LC-MS analysis of the fermentation broth suggested that ~50% of the total secreted insulin species were processed by Kex1p and Kex2p, leading to a form with the C-terminal of the B-chain extended with LG and the N-terminal of the A-chain extended with EAEA (Mw=6333). The remaining ~50% were unprocessed precursor (Mw=6628).

For proteolytic removal of the LG-extension, 100 μl fermentation broth was added 1.6 μl CPY purified from *S. cerevisiae* (~0.2 Unit). 5 μl (~0.1 Unit) DAP1 (Cathepsin C, EC 3.4.14.1) purified from Chicken Liver was added in order to remove the EAEA (SEQ ID NO:3) extension. The mixture was incubated for 200 minutes, 30° C. before LC-MS analysis. This showed that the LG-extension was completely removed, and ~75% of the EAEA (SEQ ID NO:3) extension was removed, giving the mature insulin analogue A14E, B25H-LGRREAEA (SEQ ID NO:47)-(A1-21) (Mw=5763).

Example 5

Additional insulin analogues were prepared as described in example 1. The expression yields were compared with the expression yield of the above disclosed insulin precursor MT748. All insulin analogues had the mutations A14E, B25H.

The results appear from the following table.

| $X_1$ | $X_2$ | Z | $X_3$ | $X_4$ | Yield (in percent relative to MT748) | % fully processed by KEX2 |
|---|---|---|---|---|---|---|
| LA | RR | DDLG (SEQ ID NO: 1) | KR | bond | 200.3 | >90 |
| LA | RR | DDDLG SEQ ID NO: 2) | KR | bond | 221.7 | >90 |

Example 6

Additional insulin analogues were prepared as described in example 1. In these analogues $X_1$ is LA, $X_2$ is RR, $X_3$ is KR and $X_4$ is a bond and the mutations are A14 E and B25H whereas Z is varied. The expression yields were compared with the expression yield of the above disclosed insulin precursor MT748.

The results appear from the following tables.

| Z | % yield in percent relative to MT748 | % fully processed by KEX2 |
|---|---|---|
| DADLG (SEQ ID NO: 5) | 249.2 | >90 |
| DRDLG (SEQ ID NO: 6) | 228.8 | >90 |
| DNDLG (SEQ ID NO: 7) | 232.7 | >90 |
| DCDLG (SEQ ID NO: 8) | ND | >90 |
| DQDLG (SEQ ID NO: 9) | 272.7 | >90 |
| DEDLG (SEQ ID NO: 10) | ND | >90 |
| DGDLG (SEQ ID NO: 11) | 192.1 | >90 |
| DHDLG (SEQ ID NO: 12) | 223.3 | >90 |
| DIDLG (SEQ ID NO: 13) | ND | >90 |
| DLDLG (SEQ ID NO: 14) | 216.8 | >90 |
| DKDLG (SEQ ID NO: 15) | 181.1 | >90 |
| DMDLG (SEQ ID NO: 16) | 116.9 | >90 |
| DFDLG (SEQ ID NO: 17) | 119.7 | >90 |
| DPDLG (SEQ ID NO: 18) | 237.7 | >90 |
| DSDLG (SEQ ID NO: 19) | 197.2 | >90 |
| DTDLG (SEQ ID NO: 20) | 208.7 | >90 |
| DWDLG (SEQ ID NO: 21) | 146.7 | >90 |
| DYDLG (SEQ ID NO: 22) | 211.2 | >90 |
| DVDLG (SEQ ID NO: 23) | 141.0 | >90 |
| DDALG (SEQ ID NO: 25) | 79.7 | >90 |
| DDRLG (SEQ ID NO: 26) | 277.1 | >90 |
| DDNLG (SEQ ID NO: 27) | 249.4 | >90 |
| DDCLG (SEQ ID NO: 28) | 13.9 | >90 |
| DDQLG (SEQ ID NO: 29) | 107.4 | >90 |
| DDELG (SEQ ID NO: 30) | 232.1 | >90 |
| DDGLG (SEQ ID NO: 31) | 97.0 | >90 |
| DDHLG (SEQ ID NO. 32) | 325.6 | >90 |
| DDILG (SEQ ID NO: 33) | 79.7 | >90 |
| DDLLG (SEQ ID NO: 34) | 27.7 | >90 |
| DDKLG (SEQ ID NO: 35) | 239.0 | >90 |
| DDMLG (SEQ ID NO: 36) | 110.9 | >90 |

-continued

| Z | % yield in percent relative to MT748 | % fully pro- cessed by KEX2 |
|---|---|---|
| DDFLG (SEQ ID NO: 37) | 145.5 | >90 |
| DDPLG (SEQ ID NO: 38) | 52.0 | >90 |
| DDSLG (SEQ ID NO: 39) | 256.3 | >90 |

-continued

| Z | % yield in percent relative to MT748 | % fully pro- cessed by KEX2 |
|---|---|---|
| DDTLG (SEQ ID NO: 40) | 83.1 | >90 |
| DDWLG (SEQ ID NO: 41) | 83.1 | >90 |
| DDYLG (SEQ ID NO: 42) | 65.8 | >90 |
| DDVLG (SEQ ID NO: 43) | 79.7 | >90 |

The invention claimed is:

1. A method for making mature human insulin or an analogue thereof comprising:

culturing a fungal cell comprising a DNA sequence encoding a precursor for human insulin or an analogue of human insulin, wherein the precursor comprises a B-chain of human insulin or an analogue thereof, an A-chain of human insulin or an analogue thereof, and a C-peptide linking the B-chain and the A-chain, the C peptide comprising the sequence, $X_1$-$X_2$-Z-$X_3$-$X_4$ wherein $X_1$ is a peptide sequence of 2 amino acid residues which may be the same or different and which are selected from the group consisting of Phe, Leu, Ile, Val, and Ala, $X_2$ is a Kex2 cleavage site, Z is an amino acid or a peptide sequence with from 2 to about 35 amino acid residues or a peptide bond, $X_3$ is a Kex2 cleavage site, and $X_4$ is a peptide bond, and isolating the desired product from the culture medium.

2. The method according to claim 1, wherein the first amino acid residue in the C-terminal extension of the B-chain $X_1$ counted from the N-terminal end is Leu.

3. The method according to claim 1, wherein the C-terminal extension of the B-chain $X_1$ is subsequently cleaved off by means of a carboxypeptidase giving mature human insulin or an analogue thereof.

4. The method according to claim 3, wherein the carboxypeptidase is added to the culture medium.

5. The method according to claim 1, wherein the C-peptide comprises two Kex2 cleavage sites linked by at least one amino acid residue.

6. The method according to claim 5, wherein the two Kex2 sites are linked by a peptide chain with from 1 to 5 amino acid residues which may be the same or different.

7. The method according to claim 5, wherein the two Kex2 sites are linked by a peptide chain with 3-5 amino acid residues which may be the same or different.

8. A method for making mature human insulin or an analogue thereof comprising culturing a fungal cell comprising a DNA sequence encoding a precursor for human insulin or an analogue of human insulin, wherein the precursor has the sequence B-$X_1$-$X_2$-Z-$X_3$-$X_4$-A where B is the B-chain of human insulin or an analogue thereof, A is the human insulin A chain or an analogue thereof, $X_1$ is a peptide sequence of 2 amino acid residues which may be the same or different and which are selected from the group consisting of Phe, Leu, Ile, Val, and Ala, and which will facilitate a more efficient Kex2 cleavage within the fungal cell, $X_2$ is a Kex2 cleavage site, Z is an amino acid or a peptide sequence with from 2 to about 35 amino acid residues or a peptide bond, $X_3$ is a Kex2 cleavage site, and $X_4$ is a peptide bond.

9. The method of claim 8, wherein $X_1$ in the expressed precursor can be subsequently cleaved off by a carboxypeptidase.

* * * * *

UNITED STATES PATENT AND TRADEMARK OFFICE
CERTIFICATE OF CORRECTION

| | | |
|---|---|---|
| PATENT NO. | : 8,518,668 B2 | Page 1 of 1 |
| APPLICATION NO. | : 12/311431 | |
| DATED | : August 27, 2013 | |
| INVENTOR(S) | : Norgaard et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 515 days.

Signed and Sealed this
Twenty-ninth Day of September, 2015

Michelle K. Lee
*Director of the United States Patent and Trademark Office*

SEQUENCE LISTING

```
<160> NUMBER OF SEQ ID NOS: 47

<210> SEQ ID NO 1
<211> LENGTH: 4
<212> TYPE: PRT
<213> ORGANISM: Artificial Sequence
<220> FEATURE:
<223> OTHER INFORMATION: Synthetic C-peptide

<400> SEQUENCE: 1

Asp Asp Leu Gly
1

<210> SEQ ID NO 2
<211> LENGTH: 5
<212> TYPE: PRT
<213> ORGANISM: Artificial Sequence
<220> FEATURE:
<223> OTHER INFORMATION: Synthetic C-peptide

<400> SEQUENCE: 2

Asp Asp Asp Leu Gly
1               5

<210> SEQ ID NO 3
<211> LENGTH: 4
<212> TYPE: PRT
<213> ORGANISM: Saccharomyces cerevisiae

<400> SEQUENCE: 3

Glu Ala Glu Ala
1

<210> SEQ ID NO 4
<211> LENGTH: 5
<212> TYPE: PRT
<213> ORGANISM: Artificial Sequence
<220> FEATURE:
<223> OTHER INFORMATION: Synthetic C-peptide
<220> FEATURE:
<221> NAME/KEY: MISC_FEATURE
<222> LOCATION: (2)..(2)
<223> OTHER INFORMATION: X =A, R, N, D, N, C, Q, E, G, H, I, L, K, M, F,
      P, S, T, W, Y and V.

<400> SEQUENCE: 4

Asp Xaa Asp Leu Gly
1               5
```

```
<210> SEQ ID NO 5
<211> LENGTH: 5
<212> TYPE: PRT
<213> ORGANISM: Artificial Sequence
<220> FEATURE:
<223> OTHER INFORMATION: Synthetic C-peptide

<400> SEQUENCE: 5

Asp Ala Asp Leu Gly
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic C-peptide

<400> SEQUENCE: 6

Asp Arg Asp Leu Gly
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic C-peptide

<400> SEQUENCE: 7

Asp Asn Asp Leu Gly
1               5

<210> SEQ ID NO 8
<211> LENGTH: 5
<212> TYPE: PRT
<213> ORGANISM: Artificial Sequence
<220> FEATURE:
<223> OTHER INFORMATION: Synthetic C-peptide

<400> SEQUENCE: 8

Asp Cys Asp Leu Gly
1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic C-peptide

<400> SEQUENCE: 9

Asp Gln Asp Leu Gly
1               5

<210> SEQ ID NO 10
<211> LENGTH: 5
<212> TYPE: PRT
<213> ORGANISM: Artificial Sequence
<220> FEATURE:
<223> OTHER INFORMATION: Synthetic C-peptide

<400> SEQUENCE: 10

Asp Glu Asp Leu Gly
1               5

<210> SEQ ID NO 11
<211> LENGTH: 5
```

```
<212> TYPE: PRT
<213> ORGANISM: Artificial Sequence
<220> FEATURE:
<223> OTHER INFORMATION: Synthetic C-peptide

<400> SEQUENCE: 11

Asp Gly Asp Leu Gly
1               5

<210> SEQ ID NO 12
<211> LENGTH: 5
<212> TYPE: PRT
<213> ORGANISM: Artificial Sequence
<220> FEATURE:
<223> OTHER INFORMATION: Synthetic C-peptide

<400> SEQUENCE: 12

Asp His Asp Leu Gly
1               5

<210> SEQ ID NO 13
<211> LENGTH: 5
<212> TYPE: PRT
<213> ORGANISM: Artificial Sequence
<220> FEATURE:
<223> OTHER INFORMATION: Synthetic C-peptide

<400> SEQUENCE: 13

Asp Ile Asp Leu Gly
1               5

<210> SEQ ID NO 14
<211> LENGTH: 5
<212> TYPE: PRT
<213> ORGANISM: Artificial Sequence
<220> FEATURE:
<223> OTHER INFORMATION: Synthetic C-peptide

<400> SEQUENCE: 14

Asp Leu Asp Leu Gly
1               5

<210> SEQ ID NO 15
<211> LENGTH: 5
<212> TYPE: PRT
<213> ORGANISM: Artificial Sequence
<220> FEATURE:
<223> OTHER INFORMATION: Synthetic C-peptide

<400> SEQUENCE: 15

Asp Lys Asp Leu Gly
1               5

<210> SEQ ID NO 16
<211> LENGTH: 5
<212> TYPE: PRT
<213> ORGANISM: Artificial Sequence
<220> FEATURE:
<223> OTHER INFORMATION: Synthetic C-peptide

<400> SEQUENCE: 16

Asp Met Asp Leu Gly
1               5

<210> SEQ ID NO 17
<211> LENGTH: 5
<212> TYPE: PRT
<213> ORGANISM: Artificial Sequence
```

```
<220> FEATURE:
<223> OTHER INFORMATION: Synthetic C-peptide

<400> SEQUENCE: 17

Asp Phe Asp Leu Gly
1               5

<210> SEQ ID NO 18
<211> LENGTH: 5
<212> TYPE: PRT
<213> ORGANISM: Artificial
<220> FEATURE:
<223> OTHER INFORMATION: Synthetic C-peptide

<400> SEQUENCE: 18

Asp Pro Asp Leu Gly
1               5

<210> SEQ ID NO 19
<211> LENGTH: 5
<212> TYPE: PRT
<213> ORGANISM: Artificial Sequence
<220> FEATURE:
<223> OTHER INFORMATION: Synthetic C-peptide

<400> SEQUENCE: 19

Asp Ser Asp Leu Gly
1               5

<210> SEQ ID NO 20
<211> LENGTH: 5
<212> TYPE: PRT
<213> ORGANISM: Artificial Sequence
<220> FEATURE:
<223> OTHER INFORMATION: Synthetic C-peptide

<400> SEQUENCE: 20

Asp Thr Asp Leu Gly
1               5

<210> SEQ ID NO 21
<211> LENGTH: 5
<212> TYPE: PRT
<213> ORGANISM: Artificial Sequence
<220> FEATURE:
<223> OTHER INFORMATION: Synthetic C-peptide

<400> SEQUENCE: 21

Asp Trp Asp Leu Gly
1               5

<210> SEQ ID NO 22
<211> LENGTH: 5
<212> TYPE: PRT
<213> ORGANISM: Artificial Sequence
<220> FEATURE:
<223> OTHER INFORMATION: Synthetic C-peptide

<400> SEQUENCE: 22

Asp Tyr Asp Leu Gly
1               5

<210> SEQ ID NO 23
<211> LENGTH: 5
<212> TYPE: PRT
<213> ORGANISM: Artificial Sequence
<220> FEATURE:
<223> OTHER INFORMATION: Synthetic C-peptide
```

```
<400> SEQUENCE: 23

Asp Val Asp Leu Gly
1               5

<210> SEQ ID NO 24
<211> LENGTH: 5
<212> TYPE: PRT
<213> ORGANISM: Artificial Sequence
<220> FEATURE:
<223> OTHER INFORMATION: Synthetic C-peptide
<220> FEATURE:
<221> NAME/KEY: MISC_FEATURE
<222> LOCATION: (3)..(3)
<223> OTHER INFORMATION: X = A, R, N, D, N, Q, E, G, H, I, L, K, M, F,
      P, S, T, W, Y and V.

<400> SEQUENCE: 24

Asp Asp Xaa Leu Gly
1               5

<210> SEQ ID NO 25
<211> LENGTH: 5
<212> TYPE: PRT
<213> ORGANISM: Artificial Sequence
<220> FEATURE:
<223> OTHER INFORMATION: Synthetic C-peptide

<400> SEQUENCE: 25

Asp Asp Ala Leu Gly
1               5

<210> SEQ ID NO 26
<211> LENGTH: 5
<212> TYPE: PRT
<213> ORGANISM: Artificial Sequence
<220> FEATURE:
<223> OTHER INFORMATION: Synthetic C-peptide

<400> SEQUENCE: 26

Asp Asp Arg Leu Gly
1               5

<210> SEQ ID NO 27
<211> LENGTH: 5
<212> TYPE: PRT
<213> ORGANISM: Artificial Sequence
<220> FEATURE:
<223> OTHER INFORMATION: Synthetic C-peptide

<400> SEQUENCE: 27

Asp Asp Asn Leu Gly
1               5

<210> SEQ ID NO 28
<211> LENGTH: 5
<212> TYPE: PRT
<213> ORGANISM: Artificial Sequence
<220> FEATURE:
<223> OTHER INFORMATION: Synthetic C-peptide

<400> SEQUENCE: 28

Asp Asp Cys Leu Gly
1               5

<210> SEQ ID NO 29
<211> LENGTH: 5
<212> TYPE: PRT
```

```
<213> ORGANISM: Artificial Sequence
<220> FEATURE:
<223> OTHER INFORMATION: Synthetic C-peptide

<400> SEQUENCE: 29

Asp Asp Gln Leu Gly
1               5

<210> SEQ ID NO 30
<211> LENGTH: 5
<212> TYPE: PRT
<213> ORGANISM: Artificial Sequence
<220> FEATURE:
<223> OTHER INFORMATION: Synthetic C-peptide

<400> SEQUENCE: 30

Asp Asp Glu Leu Gly
1               5

<210> SEQ ID NO 31
<211> LENGTH: 5
<212> TYPE: PRT
<213> ORGANISM: Artificial Sequence
<220> FEATURE:
<223> OTHER INFORMATION: Synthetic C-peptide

<400> SEQUENCE: 31

Asp Asp Gly Leu Gly
1               5

<210> SEQ ID NO 32
<211> LENGTH: 5
<212> TYPE: PRT
<213> ORGANISM: Artificial Sequence
<220> FEATURE:
<223> OTHER INFORMATION: Synthetic C-peptide

<400> SEQUENCE: 32

Asp Asp His Leu Gly
1               5

<210> SEQ ID NO 33
<211> LENGTH: 5
<212> TYPE: PRT
<213> ORGANISM: Artificial Sequence
<220> FEATURE:
<223> OTHER INFORMATION: Synthetic C-peptide

<400> SEQUENCE: 33

Asp Asp Ile Leu Gly
1               5

<210> SEQ ID NO 34
<211> LENGTH: 5
<212> TYPE: PRT
<213> ORGANISM: Artificial Sequence
<220> FEATURE:
<223> OTHER INFORMATION: Synthetic C-peptide

<400> SEQUENCE: 34

Asp Asp Leu Leu Gly
1               5

<210> SEQ ID NO 35
<211> LENGTH: 5
<212> TYPE: PRT
<213> ORGANISM: Artificial
<220> FEATURE:
```

<223> OTHER INFORMATION: Synthetic C-peptide

<400> SEQUENCE: 35

Asp Asp Lys Leu Gly
1               5

<210> SEQ ID NO 36
<211> LENGTH: 5
<212> TYPE: PRT
<213> ORGANISM: Artificial Sequence
<220> FEATURE:
<223> OTHER INFORMATION: Synthetic C-peptide

<400> SEQUENCE: 36

Asp Asp Met Leu Gly
1               5

<210> SEQ ID NO 37
<211> LENGTH: 5
<212> TYPE: PRT
<213> ORGANISM: Artificial Sequence
<220> FEATURE:
<223> OTHER INFORMATION: Synthetic C-peptide

<400> SEQUENCE: 37

Asp Asp Phe Leu Gly
1               5

<210> SEQ ID NO 38
<211> LENGTH: 5
<212> TYPE: PRT
<213> ORGANISM: Artificial Sequence
<220> FEATURE:
<223> OTHER INFORMATION: Synthetic C-peptide

<400> SEQUENCE: 38

Asp Asp Pro Leu Gly
1               5

<210> SEQ ID NO 39
<211> LENGTH: 5
<212> TYPE: PRT
<213> ORGANISM: Artificial Sequence
<220> FEATURE:
<223> OTHER INFORMATION: Synthetic C-peptide

<400> SEQUENCE: 39

Asp Asp Ser Leu Gly
1               5

<210> SEQ ID NO 40
<211> LENGTH: 5
<212> TYPE: PRT
<213> ORGANISM: Artificial Sequence
<220> FEATURE:
<223> OTHER INFORMATION: Synthetic C-peptide

<400> SEQUENCE: 40

Asp Asp Thr Leu Gly
1               5

<210> SEQ ID NO 41
<211> LENGTH: 5
<212> TYPE: PRT
<213> ORGANISM: Artificial Sequence
<220> FEATURE:
<223> OTHER INFORMATION: Synthetic C-peptide

```
<400> SEQUENCE: 41

Asp Asp Trp Leu Gly
1               5

<210> SEQ ID NO 42
<211> LENGTH: 5
<212> TYPE: PRT
<213> ORGANISM: Artificial Sequence
<220> FEATURE:
<223> OTHER INFORMATION: Synthetic C-peptide

<400> SEQUENCE: 42

Asp Asp Tyr Leu Gly
1               5

<210> SEQ ID NO 43
<211> LENGTH: 5
<212> TYPE: PRT
<213> ORGANISM: Artificial Sequence
<220> FEATURE:
<223> OTHER INFORMATION: Synthetic C-peptide

<400> SEQUENCE: 43

Asp Asp Val Leu Gly
1               5

<210> SEQ ID NO 44
<211> LENGTH: 205
<212> TYPE: DNA
<213> ORGANISM: Homo sapiens

<400> SEQUENCE: 44
ccatggctaa gagattcgtt aaccaacact tgtgcggttc ccacttggtt gaagctttgt    60
acttggtttg cggtgaaaga ggtttccact acactcctaa gactctagcg agaagagact   120
tgggtaagag aggtattgtc gaacaatgct gtacatcgat atgctccttg gaacaattgg   180
aaaactactg caactagact ctaga                                         205

<210> SEQ ID NO 45
<211> LENGTH: 9
<212> TYPE: PRT
<213> ORGANISM: Artificial Sequence
<220> FEATURE:
<223> OTHER INFORMATION: Synthetic C-peptide

<400> SEQUENCE: 45

Leu Ala Arg Arg Asp Leu Gly Lys Arg
1               5

<210> SEQ ID NO 46
<211> LENGTH: 59
<212> TYPE: PRT
<213> ORGANISM: Homo sapiens

<400> SEQUENCE: 46

Ser Met Ala Lys Arg Phe Val Asn Gly His Leu Cys Gly Ser His Leu
1               5                   10                  15

Val Glu Ala Leu Tyr Leu Val Cys Gly Glu Arg Gly Phe His Tyr Thr
                20                  25                  30

Pro Lys Thr Leu Ala Arg Arg Asp Leu Gly Lys Arg Gly Ile Val Glu
            35                  40                  45

Gln Cys Cys Thr Ser Ile Cys Ser Leu Glu Gln
        50                  55
```

```
<210> SEQ ID NO 47
<211> LENGTH: 8
<212> TYPE: PRT
<213> ORGANISM: Artificial Sequence
<220> FEATURE:
<223> OTHER INFORMATION: Synthetic C-peptide

<400> SEQUENCE: 47

Leu Gly Arg Arg Glu Ala Glu Ala
1               5
```